United States Patent
Li

(10) Patent No.: US 7,265,092 B2
(45) Date of Patent: Sep. 4, 2007

(54) PHARMACEUTICAL FORMULATION

(75) Inventor: Mike Tso-ping Li, Cupertino, CA (US)

(73) Assignee: KAI Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 11/240,962

(22) Filed: Sep. 30, 2005

(65) Prior Publication Data

US 2006/0153867 A1 Jul. 13, 2006

Related U.S. Application Data

(60) Provisional application No. 60/615,486, filed on Sep. 30, 2004.

(51) Int. Cl.
*A61K 38/00* (2006.01)
(52) U.S. Cl. .......................... 514/13; 530/326
(58) Field of Classification Search .................. None
See application file for complete search history.

(56) References Cited

U.S. PATENT DOCUMENTS

| | | | |
|---|---|---|---|
| 4,847,240 A | 7/1989 | Ryser et al. | |
| 5,652,122 A | 7/1997 | Frankel et al. | |
| 5,670,617 A | 9/1997 | Frankel et al. | |
| 5,674,980 A | 10/1997 | Frankel et al. | |
| 5,747,641 A | 5/1998 | Frankel et al. | |
| 5,783,405 A | 7/1998 | Mochly-Rosen et al. | |
| 5,804,604 A | 9/1998 | Frankel et al. | |
| 5,888,762 A | 3/1999 | Joliot et al. | |
| 6,165,977 A | 12/2000 | Mochly-Rosen | |
| 6,316,003 B1 | 11/2001 | Frankel et al. | |
| 6,593,292 B1 | 7/2003 | Rothbard et al. | |
| 6,855,693 B2 | 2/2005 | Mochly-Rosen et al. | |
| 6,933,275 B2 | 8/2005 | Mochly-Rosen et al. | |
| 2002/0057413 A1 | 5/2002 | Sumida et al. | |
| 2002/0150984 A1 | 10/2002 | Mochly-Rosen et al. | |
| 2002/0168354 A1* | 11/2002 | Mochly-Rosen | ........... 424/94.5 |
| 2003/0104622 A1 | 6/2003 | Robbins et al. | |
| 2003/0199677 A1 | 10/2003 | Avrameas et al. | |
| 2003/0206900 A1 | 11/2003 | Ternynck et al. | |
| 2003/0223981 A1 | 12/2003 | Mochly-Rosen et al. | |
| 2004/0009922 A1 | 1/2004 | Mochly-Rosen | |
| 2004/0204364 A1 | 10/2004 | Mochly-Rosen et al. | |

OTHER PUBLICATIONS

Shizukuda, et al., Am. J. Physiol Heart Circ Physiol, 2002, 282, H1625-H1634.*

* cited by examiner

*Primary Examiner*—Anish Gupta
*Assistant Examiner*—Satyanarayana R. Gudibande
(74) *Attorney, Agent, or Firm*—Morrison & Foerster LLP

(57) ABSTRACT

A pharmaceutical formulation for a PKC modulatory peptide and a transport moiety comprising the aforementioned components and an anti-aggregant.

8 Claims, 1 Drawing Sheet

PHARMACEUTICAL FORMULATION

RELATED APPLICATION

This application claims benefit of U.S. application Ser. No. 60/615,486 filed Sep. 30, 2004 which is hereby incorporated by reference in its entirety.

TECHNICAL FIELD

This invention relates to pharmaceutical formulations, particularly to formulations of amino acids, peptides and small proteins, and specifically to formulations for PKC peptide/transporter conjugates.

BACKGROUND ART

Protein kinase C ("PKC") is a key enzyme in signal transduction involved in a variety of cellular functions, including cell growth, regulation of gene expression, and ion channel activity. The PKC family of isozymes includes at least 10 different protein kinases that can be divided into at least three subfamilies based on their homology and sensitivity to activators. (See FIG. 1.) Each isozyme includes a number of homologous ("conserved" or "C") domains interspersed with isozyme-unique ("variable" or "V") domains. Members of the "classical" subfamily, α (SEQ ID NO:164), $β_I$ (SEQ ID NO:165), $β_{II}$ (SEQ ID NO:166) and γPKC (SEQ ID NO:167), contain four homologous domains (C1, C2, C3 and C4) and require calcium, phosphatidylserine, and diacylglycerol or phorbol esters for activation. Members of the "novel" subfamily, δ(SEQ ID NO:168), ε (SEQ ID NO:169), η (SEQ ID NO:170) and θPKC (SEQ ID NO:171), lack the C2 homologous domain and do not require calcium for activation. Finally, members of the "atypical" subfamily, ζ (SEQ ID NO:174) and λ/ιPKC (SEQ ID NO:172), lack both the C2 and one-half of the C1 homologous domains and are insensitive to diacylglycerol, phorbol esters and calcium.

Individual isozymes of PKC have been implicated in the mechanisms of various disease states, including the following: cancer (alpha and delta PKC); cardiac hypertrophy and heart failure (beta I and beta II PKC) nociception (gamma and epsilon PKC); ischemia including myocardial infarction (delta and epsilon PKC); immune response, particularly T-cell mediated (theta PKC); and fibroblast growth and memory (zeta PKC).

DISCLOSURE OF THE INVENTION

In accordance with the objects outlined above, the disclosed invention provides a pharmaceutical formulation for a protein kinase C modulatory peptide and a cationic (i.e., positively charged) transport peptide and an anti-aggregant. A preferred anti-aggregant is a sugar characterized by having a sufficient number stereochemically aligned hydroxyl moieties to interact with the modulatory peptide and/or the transport peptide hydrophobic and/or positively charged portions so as to favor their organization with the anti-aggregant, rather than aggregation with each other. PKC modulatory peptides, such as peptides derived from various PKC variable regions, comprise preferred embodiments. Cationic transport moieties useful in the invention include cationic peptides, such as poly-arginine and HIV-tat. A particularly preferred embodiment comprises a PKC inhibitory peptide and a HIV-tat derived transport peptide. An example of such an embodiment is KAI-9803 (SEQ ID NO:1).

In one of the particular aspects of the above-described pharmaceutical formulation, the ratio of anti-aggregant to peptide/transporter conjugate ranges from about 100:1 to about 1:1, 90:1, 80:1, 70:1, 60:1, 50:1, 40:1, 30:1, 20:1, 10:1, 5:1, and 1:1.

Another aspect of the invention provides a stable pharmaceutical product for shipping and storing prior to use, including a lyophilized cake of KAI-9803 and an anti-aggregant in a sealed container. The lyophilized product is preferably obtained from a solution of KAI-9803 plus acetate counterion. The ratio of KAI-9803 to anti-aggregant is from about 1:5 to about 1:100, particularly about 1:80 and especially about 1:8. The anti-aggregant is preferably a sugar. One specific such product is 5 mg KAI-9803 and 40 mg mannitol in a stoppered glass vial. Instructions for reconstitution are preferably incorporated on the container or its attached label, outer packaging and/or package insert.

Another aspect of the invention provides a formulation for parenteral (particularly intracoronary) administration that is about 2.5 mg/mL KAI-9803 and about 20 mg/mL mannitol reconstituted from a lyophilized cake using sodium chloride for injection, USP (preferably 0.9%) to a concentration ranging from about 0.001 to 2.5 mg/mL, preferably about 0.01 to 1.0 mg/mL. To reconstitute the lyophilized formulation for administration, a sealed container of product is first warmed to about room temperature, after which a pharmaceutically acceptable solvent (such as saline, preferably 9% saline) is added in an amount sufficient to solubilize the lyophilized cake, followed by the addition of such additional quantity of solvent as is necessary to obtain a desired concentration for administration.

Still another aspect of the invention is a method of manufacture, including the steps:

(a) Appropriate amounts of anti-aggregant, hydrophobic active agent and/or cationic transport moiety are introduced to a suitably sized container (preferably a glass vial) as dry solids.

(B) A pharmaceutically acceptable solvent is added to the container in an amount sufficient to dissolve the solids.

(C) The solution thus-formed is lyophilized to dryness.

(D) The container is sealed (optionally after first filling the head-space with a non-reactive gas, such as nitrogen).

Other aspects and embodiments will be apparent to those skilled in the art form the following detailed description.

MODES OF CARRYING OUT THE INVENTION

Figure 1:
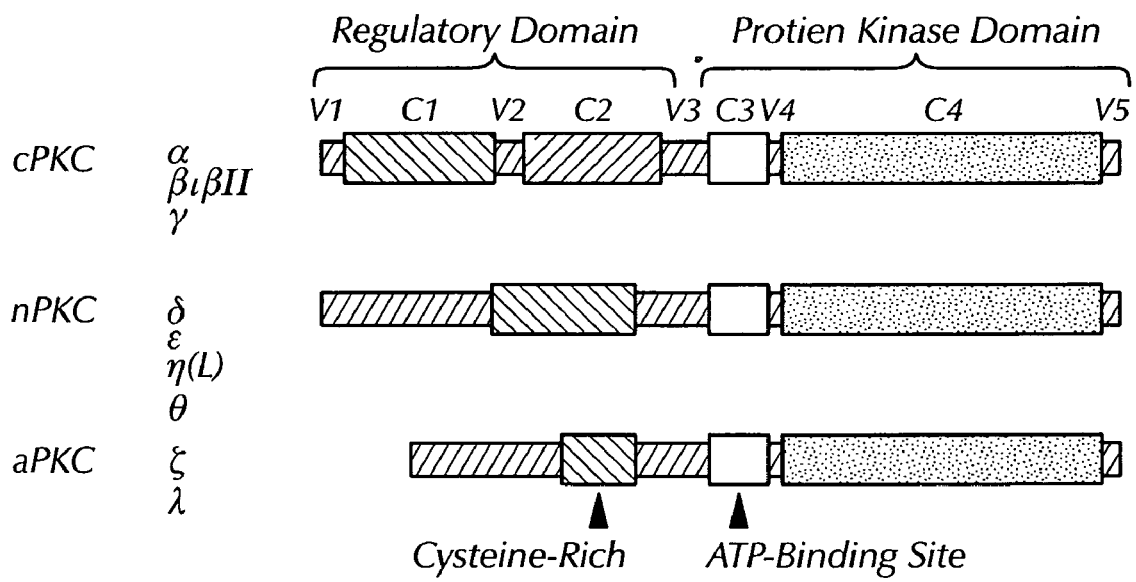
FIG. 1 shows a schematic of the three families of protein kinase C isozymes.

The presently described invention relates to pharmaceutical formulations of peptides which modulate the activity of one or more protein kinase C isozymes. In certain embodiments, the peptides discussed herein are coupled to a carrier moiety to facilitate transport of the modulatory peptide to a target cell. Typically, preferred embodiments of the disclosed pharmaceutical formulations further comprise an anti-aggregant and one or more excipients. The pharmaceutical formulations comprising the modulatory peptides provide advantages in the handling of the active pharmaceutical ingredients, in formulation manufacture, stability, concentration and ease of use. These and other advantages are described in greater detail below.

DEFINITIONS

As used in the present, specification, the following words and phrases are generally intended to have the meanings as set forth below, except to the extent that the context in which they are used indicates otherwise.

A "PKC modulatory peptide" or "a peptide which modulate the activity of one or more protein kinase C isozymes" refer to a peptide that can promote, enhance or activate one or more PKC isozymes, or alternatively the peptide can also inhibit or inactivate one or more PKC isozymes.

The term "API" means active pharmaceutical ingredient, which as used herein refers to a PKC modulatory peptide and a transport moiety, covalently bound to one another, and/or one or more active agents.

The term "disorder" or "disease state" means any mammalian disease, condition, symptom, or indication, preferably arising in a human patient.

The term "effective amount" refers to that amount of an API that is sufficient to effect treatment, as defined below, when administered to a mammal in need of such treatment.

The term "KAI-9803" refers to an peptide derived from the first variable region of δPKC conjugated via a Cys-Cys disulfide linkage to a HIV Tat-derived transporter peptide, and can be represented as follows:

acid, cinnamic acid, mandelic acid, methanesulfonic acid, ethanesulfonic acid, p-toluene-sulfonic acid, salicylic acid, and the like.

The term "pharmaceutical product" refers to an API, formulated and filled into a container for storage, transportation, or administration.

The term "PKC-derived peptide" refers to a PKC isozyme- and/or variable region-specific peptides as described, for example, in U.S. Patents and Publications U.S. Pat. Nos. 5,783,405, 6,165,977, US2002/0150984, US2002/0168354, US2002/057413, US2003/0223981, US2004/0009922 and in copending U.S. provisional application Ser. No. 60/550,755, filed Mar. 5, 2004, all of which are hereby incorporated by reference in their entirety.

The term "transporter moiety" means a component of an API that facilitates cellular uptake, such as cationic polymers, peptides and antibody sequences, including polylysine, polyarginine, Antennapedia-derived peptides, HIV Tat-derived peptides and the like. An example of a transporter moiety is a "transporter peptide", which is a peptide which facilitates cellular uptake of a PKC modulating peptide which is chemically associated or bonded to the transporter peptide.

The term "treatment" or "treating" means any treatment of a disease or disorder in a mammal, including: preventing

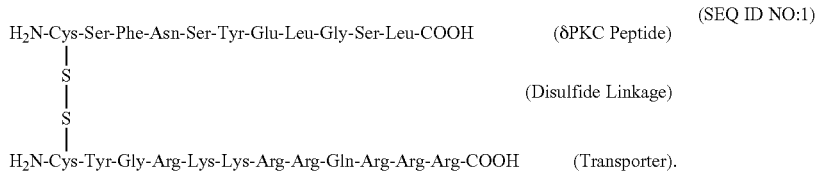

The term "optional" or "optionally" means that the subsequently described event or circumstance may or may not occur, and that the description includes instances where such event or circumstance occurs and instances in which it does not.

As used herein, "pharmaceutically acceptable carrier" or "pharmaceutically acceptable excipient" includes any and all solvents, dispersion media, antibacterial and antifungal agents, isotonic and absorption delaying agents and the like. The use of such media and agents for pharmaceutically active substances is well known in the art. Supplementary active ingredients can also be incorporated into the compositions.

The term "pharmaceutically acceptable salt" or "counterion" refers to salts which retain the biological effectiveness and properties of the API and which are not biologically or otherwise undesirable. In many cases, the API will be capable of forming acid and/or base salts by virtue of the presence of amino and/or carboxyl groups or groups similar thereto. Pharmaceutically acceptable base addition salts can be prepared from inorganic and/or organic bases. Pharmaceutically acceptable acid addition salts may be prepared from inorganic and/or organic acids. For example, inorganic acids include hydrochloric acid, hydrobromic acid, sulfuric acid, nitric acid, phosphoric acid, and the like. Organic acids include acetic acid, propionic acid, glycolic acid, pyruvic acid, oxalic acid, malic acid, malonic acid, succinic acid, maleic acid, fumaric acid, tartaric acid, citric acid, benzoic or protecting against the disease or disorder, that is, causing the clinical symptoms not to develop; inhibiting the disease or disorder, that is, arresting or suppressing the development of clinical symptoms; and/or relieving the disease or disorder, that is, causing the regression of clinical symptoms.

The term "prophylaxis" is intended as an element of "treatment" to encompass both "preventing" and "suppressing" as defined herein. It will be understood by those skilled in the art that in human medicine it is not always possible to distinguish between "preventing" and "suppressing" since the ultimate inductive event or events may be unknown, latent, or the patient is not ascertained until well after the occurrence of the event or events.

Protein Kinase C Modulatory Peptides

Various PKC isozyme- and variable region-specific peptides have been described and can be used with the presently disclosed invention. Preferably, the PKC modulatory peptide is a V1, V3 or V5-derived peptide. The following US Patents or Patent Applications describe a variety of suitable peptides that can be used with the presently disclosed invention: U.S. Pat. Nos. 5,783,405, 6,165,977, 6,855,693, US2004/0204364, US2002/0150984, US2002/0168354, US2002/057413, US2003/0223981, US2004/0009922 and Ser. No. 10/428,280, each of which are incorporated herein by reference in their entirety. Table 1 provides a listing of preferred PKC modulatory peptides for use with the present invention.

TABLE 1

Peptides derived from PKC isozymes

| Peptide | SEQ ID NO. | Sequence |
|---|---|---|
| αV3-1 | SEQ ID NO:2 | I-P-E-G-D-E-E-G |
| αV5-1 | SEQ ID NO:3 | Q-L-V-I-A-N |
| αV5-1.1 | SEQ ID NO:4 | G-L-G-A-E-N |
| αV5-1.2 | SEQ ID NO:5 | A-R-G-A-E-N |
| αV5-1.3 | SEQ ID NO:6 | C-G-K-G-A-E-N |
| αV5-1.4 | SEQ ID NO:7 | C-G-K-G-A-E-N |
| βC2-1 | SEQ ID NO:8 | K-Q-K-T-K-T-I-K |
| βC2-2 | SEQ ID NO:9 | M-D-P-N-G-L-S-D-P-Y-V-K-L |
| βC2-3 | SEQ ID NO:10 | I-P-D-P-K-S-E |
| βC2-4 | SEQ ID NO:11 | S-L-N-P-E-W-N-E-T |
| βV3-1 | SEQ ID NO:12 | V-P-P-E-G-S-E-A |
| βIV5-1 | SEQ ID NO:13 | K-L-F-I-M-N |
| βIV5-2 | SEQ ID NO:14 | R-D-K-R-D-T-S |
| βIV5-2.1 | SEQ ID NO:15 | C-A-R-D-K-R-D-T-S |
| βIV5-2.2 | SEQ ID NO:16 | G-R-D-K-R-D-T-S |
| βIV5-2.3 | SEQ ID NO:17 | A-R-D-K-R-D-T-S |
| βIV5-3 | SEQ ID NO:18 | A-R-D-K-R-D-T-S-N-F-D-K |
| βIV5-4 | SEQ ID NO:19 | A-G-F-S-Y-T-N-P-E-F-V-I-N-V |
| βIIV5-1 | SEQ ID NO:20 | Q-E-V-I-R-N |
| βIIV5-2 | SEQ ID NO:21 | C-G-R-N-A-E |
| βIIV5-3 | SEQ ID NO:22 | A-C-G-R-N-A-E |
| βIIV5-3.1 | SEQ ID NO:23 | A-C-G-K-N-A-E |
| βIIV5-4 | SEQ ID NO:24 | K-A-C-G-R-N-A-E |
| βIIV5-5 | SEQ ID NO:25 | C-G-R-N-A-E-N |
| βIIV5-6 | SEQ ID NO:26 | A-C-G-R-N-A-E |
| βIIV5-7 | SEQ ID NO:27 | S-F-V-N-S-E-F-L-K-P-E-V-L-S |
| γV3-1 | SEQ ID NO:28 | V-A-D-A-D-N-C-S |
| γV5-1 | SEQ ID NO:29 | G-R-S-G-E-N |
| γV5-1.1 | SEQ ID NO:30 | G-L-S-G-E-N |
| γV5-2 | SEQ ID NO:31 | R-L-V-L-A-S |
| γV5-3 | SEQ ID NO:32 | P-C-G-R-S-G-E-N |
| δV1-1 | SEQ ID NO:33 | C-S-F-N-S-Y-E-L-G-S-L |
| δV1-1.1 | SEQ ID NO:34 | S-F-N-S-Y-E-L-G-S-L |
| δV1-1.2 | SEQ ID NO:35 | T-F-N-S-Y-E-L-G-S-L |
| δV1-1.3 | SEQ ID NO:36 | A-F-N-S-N-Y-E-L-G-S-L |
| δV1-1.4 | SEQ ID NO:37 | S-F-N-S-Y-E-L-G-T-L |
| δV1-1.5 | SEQ ID NO:38 | S-T-N-S-Y-E-L-G-S-L |
| δV1-1.6 | SEQ ID NO:39 | S-F-N-S-F-E-L-G-S-L |
| δV1-1.7 | SEQ ID NO:40 | S-N-S-Y-D-L-G-S-L |
| δV1-1.8 | SEQ ID NO:41 | S-F-N-S-Y-E-L-P-S-L |
| δV1-1.9 | SEQ ID NO:42 | T-F-N-S-Y-E-L-G-T-L |
| δV1-1.10 | SEQ ID NO:43 | S-F-N-S-Y-E-I-G-S-V |
| δV1-1.11 | SEQ ID NO:44 | S-F-N-S-Y-E-V-G-S-I |
| δV1-1.12 | SEQ ID NO:45 | S-F-N-S-Y-E-L-G-S-V |
| δV1-1.13 | SEQ ID NO:46 | S-F-N-S-Y-E-L-G-S-I |
| δV1-1.14 | SEQ ID NO:47 | S-F-N-S-Y-E-I-G-S-L |
| δV1-1.15 | SEQ ID NO:48 | S-F-N-S-Y-E-V-G-S-L |
| δV1-1.16 | SEQ ID NO:49 | A-F-N-S-Y-E-L-G-S-L |
| δV1-1.17 | SEQ ID NO:50 | Y-D-L-G-S-L |
| δV1-1.18 | SEQ ID NO:51 | F-D-L-G-S-L |
| δV1-1.19 | SEQ ID NO:52 | Y-D-I-G-S-L |
| δV1-1.20 | SEQ ID NO:53 | Y-D-V-G-S-L |
| δV1-1.21 | SEQ ID NO:54 | Y-D-L-P-S-L |
| δV1-1.22 | SEQ ID NO:55 | Y-D-L-G-L-L |
| δV1-1.23 | SEQ ID NO:56 | Y-D-L-G-S-I |
| δV1-1.24 | SEQ ID NO:57 | Y-D-L-G-S-V |
| δV1-1.25 | SEQ ID NO:58 | I-G-S-L |
| δV1-1.26 | SEQ ID NO:59 | V-G-S-L |
| δV1-1.27 | SEQ ID NO:60 | L-P-S-L |
| δV1-1.28 | SEQ ID NO:61 | L-G-L-L |
| δV1-1.29 | SEQ ID NO:62 | L-G-S-I |
| δV1-1.30 | SEQ ID NO:63 | L-G-S-V |
| δV1-2 | SEQ ID NO:64 | A-L-S-T-E-R-G-K-T-L-V |
| δV1-2.1 | SEQ ID NO:65 | A-L-S-T-D-R-G-K-T-L-V |
| δV1-2.2 | SEQ ID NO:66 | A-L-T-S-D-R-G-K-T-L-V |
| δV1-2.3 | SEQ ID NO:67 | A-L-T-T-D-R-G-K-S-L-V |
| δV1-2.4 | SEQ ID NO:68 | A-L-T-T-D-R-P-K-T-L-V |
| δV1-2.5 | SEQ ID NO:69 | A-L-T-T-D-R-G-R-T-L-V |
| δV1-2.6 | SEQ ID NO:70 | A-L-T-D-K-G-K-T-L-V |
| δV1-2.7 | SEQ ID NO:71 | A-L-T-T-D-K-G-K-T-L-V |
| δV1-3 | SEQ ID NO:72 | V-L-M-R-A-A-E-E-P-V |
| δV1-4 | SEQ ID NO:73 | Q-S-M-R-S-E-D-E-A-K |
| δV1-5 | SEQ ID NO:163 | A-F-N-S-Y-E-L-G-S |
| δV3-1 | SEQ ID NO:74 | Q-G-F-E-K-K-T-G-V |
| δV3-2 | SEQ ID NO:75 | D-N-N-G-T-Y-G-K-I |

TABLE 1-continued
Peptides derived from PKC isozymes

| Peptide | SEQ ID NO. | Sequence |
|---|---|---|
| δV5-1 | SEQ ID NO:76 | K-N-L-I-D-S |
| δV5-2 | SEQ ID NO:77 | V-K-S-P-R-D-Y-S |
| δV5-2.1 | SEQ ID NO:78 | V-K-S-P-C-R-D-Y-S |
| δV5-2.2 | SEQ ID NO:79 | I-K-S-P-R-L-Y-S |
| δV5-3 | SEQ ID NO:80 | K-N-L-I-D-S |
| δV5-4 | SEQ ID NO:81 | P-K-V-K-S-P-R-D-Y-S-N |
| εV1-1 | SEQ ID NO:82 | N-G-L-L-K-I-K |
| εV1-2 | SEQ ID NO:83 | E-A-V-S-L-K-P-T |
| εV1-3 | SEQ ID NO:84 | L-A-V-F-H-D-A-P-I-G-Y |
| εV1-4 | SEQ ID NO:85 | D-D-F-V-A-N-C-T-I |
| εV1-5 | SEQ ID NO:86 | W-I-D-L-E-P-E-G-R-V |
| εV1-6 | SEQ ID NO:87 | H-A-V-G-P-R-P-Q-T-F |
| εV1-7 | SEQ ID NO:88 | N-G-S-R-H-F-E-D |
| εV1-7.1 | SEQ ID NO:89 | H-D-A-P-I-G-D-Y |
| εV1-7.2 | SEQ ID NO:90 | H-D-A-P-I-G |
| εV1-7.3 | SEQ ID NO:91 | H-D-A-A-I-G-Y-D |
| εV1-7.4 | SEQ ID NO:92 | H-D-A-P-I-P-Y-D |
| εV1-7.5 | SEQ ID NO:93 | H-N-A-P-I-G-Y-D |
| εV1-7.6 | SEQ ID NO:94 | H-A-A-P-I-G-Y-D |
| εV1-7.7 | SEQ ID NO:95 | A-D-A-P-I-G-Y-D |
| εV1-7.8 | SEQ ID NO:96 | H-D-A-P-A-G-Y-D |
| εV1-7.9 | SEQ ID NO:97 | H-D-A-P-I-G-A-D |
| εV1-7.10 | SEQ ID NO:98 | H-D-A-P-I-A-Y-D |
| εV1-7.11 | SEQ ID NO:99 | H-D-A-P-I-G-Y-A |
| εV3-1 | SEQ ID NO:100 | S-S-P-S-E-E-D-R-S |
| εV3-2 | SEQ ID NO:101 | P-C-D-Q-E-I-K-E |
| εV3-3 | SEQ ID NO:102 | E-N-N-I-R-K-A-L-S |
| εV3-4 | SEQ ID NO:103 | G-E-V-R-Q-G-Q-A |
| εV5-1 | SEQ ID NO:104 | E-A-I-V-K-Q |
| εV5-2 | SEQ ID NO:105 | I-K-T-K-R-D-V |
| εV5-2.1 | SEQ ID NO:106 | I-K-T-K-R-L-I |
| εV5-3 | SEQ ID NO:107 | C-E-A-I-V-K-Q |
| εV5-4 | SEQ ID NO:108 | T-K-R-D-V-N-N-F-D-Q |
| ζV1-1 | SEQ ID NO:109 | V-R-L-K-A-H-Y |
| ζV1-2 | SEQ ID NO:110 | V-D-S-E-G-D |
| ζV1-3 | SEQ ID NO:111 | V-F-P-S-I-P-E-Q |
| ζV3-1 | SEQ ID NO:112 | S-Q-E-P-P-V-D-D-K-N-E-D-A-D-L |
| ζV3-2 | SEQ ID NO:113 | I-K-D-D-S-E-D |
| ζV3-3 | SEQ ID NO:114 | P-V-I-D-G-M-D-G-I |
| ζV5-1 | SEQ ID NO:115 | E-D-A-I-K-R |
| ζV5-1.1 | SEQ ID NO:116 | E-D-A-I-R |
| ζV5-2 | SEQ ID NO:117 | I-T-D-D-Y-G-L-D |
| ζV5-2.1 | SEQ ID NO:118 | I-T-D-D-Y-G-L |
| ζV5-3 | SEQ ID NO:119 | D-D-Y-G-L-D-N |
| ηV1-1 | SEQ ID NO:120 | N-G-Y-L-R-V-R |
| ηV1-2 | SEQ ID NO:121 | E-A-V-G-L-Q-P-T |
| ηV1-3 | SEQ ID NO:122 | L-A-V-F-H-E-T-P-L-G-Y |
| ηV1-4 | SEQ ID NO:123 | D-F-V-A-N-C-T-L |
| ηV1-5 | SEQ ID NO:124 | W-V-D-L-E-P-E-G-K-V |
| ηV1-6 | SEQ ID NO:125 | H-S-L-F-K-K-G-H |
| ηV1-7 | SEQ ID NO:126 | T-G-A-S-D-T-F-E-G |
| ηV5-1 | SEQ ID NO:127 | E-G-H-L-P-M |
| ηV5-1.1 | SEQ ID NO:128 | E-G-H-D-P-M |
| ηV5-2 | SEQ ID NO:129 | I-K-S-R-E-D-V-S |
| ηV5-3 | SEQ ID NO:130 | V-R-S-R-E-D-V-S |
| ηV5-4 | SEQ ID NO:131 | P-R-I-K-S-R-E-D-V |
| λV1-1 | SEQ ID NO:132 | H-Q-V-R-V-K-A-Y-Y-R |
| λV1-2 | SEQ ID NO:133 | Y-E-L-N-K-D-S-E-L-L-I |
| λV3-1 | SEQ ID NO:134 | M-D-Q-S-S-M-H-S-D-H-A-Q-T-V-I |
| λV3-2 | SEQ ID NO:135 | L-D-Q-V-G-E-E |
| λV3-3 | SEQ ID NO:136 | E-A-M-N-T-R-E-S-G |
| λV5-1 | SEQ ID NO:137 | D-D-I-V-R-K |
| μV5-2 | SEQ ID NO:138 | V-K-L-C-D-F-G-F |
| μV5-2.1 | SEQ ID NO:139 | I-R-L-C-D-F-A-F |
| μV5-3 | SEQ ID NO:140 | Q-V-K-L-C-D-F-G-F-A |
| μV1-1 | SEQ ID NO:141 | M-S-V-P-P-L-L-R-P |
| μV1-2 | SEQ ID NO:142 | K-F-P-E-C-G-F-Y-G-L-Y |
| μV3-1 | SEQ ID NO:143 | D-P-D-A-D-Q-E-D-S |
| μV3-2 | SEQ ID NO:144 | S-K-D-T-L-R-K-R-H |
| μV3-3 | SEQ ID NO:145 | I-T-L-F-Q-N-D-T-G |
| μV3-4 | SEQ ID NO:146 | G-S-N-S-H-K-D-I-S |
| μV5-1 | SEQ ID NO:147 | S-D-S-P-E-A |
| ΘV1-1 | SEQ ID NO:148 | G-L-S-N-F-D-C-G |
| ΘV1-2 | SEQ ID NO:149 | Y-V-E-S-E-N-G-Q-M-Y-I |

TABLE 1-continued

Peptides derived from PKC isozymes

| Peptide | SEQ ID NO. | Sequence |
|---|---|---|
| ΘV1-3 | SEQ ID NO:150 | I-V-K-G-K-N-V-D-L-I |
| ΘV1-4 | SEQ ID NO:151 | D-M-N-E-F-E-T-E-G-F |
| ΘV3-1 | SEQ ID NO:152 | C-S-I-K-N-E-A-R-L |
| ΘV3-2 | SEQ ID NO:153 | G-K-R-E-P-Q-G-I-S |
| ΘV3-3 | SEQ ID NO:154 | D-E-V-D-K-M-C-H-L |
| ΘV5-1 | SEQ ID NO:155 | R-A-L-I-N-S |
| ΘV5-2 | SEQ ID NO:156 | V-K-S-P-F-D-C-S |
| ΘV5-2.1 | SEQ ID NO:157 | V-R-S-P-F-D-C-S |
| ΘV5-3 | SEQ ID NO:158 | D-R-A-L-I-N-S |
| ιV5-1 | SEQ ID NO:159 | I-S-G-E-F-G-L-D |
| ιV5-1.1 | SEQ ID NO:160 | C-S-G-E-F-G-L-D |
| ιV5-2 | SEQ ID NO:161 | D-D-D-I-V-R-K |
| ιV5-3 | SEQ ID NO:162 | D-D-I-V-R-K |

As discussed more fully below, it is preferable that the PKC modulatory peptide be chemically associated with a transport peptide. In a particularly preferred embodiment, the modulatory peptide and the transport peptide are linked via a disulfide bond. In the case of the forming a disulfide bond, it may be advantageous to add Cys residue to the PKC modulatory peptide sequence, preferably at the amino terminus of the peptide. Alternatively, an endogenous Cys residue can be exploited to link the modulatory peptide with the transport peptide or moiety. Methods of forming disulfide bonds are well known to those of ordinary skill in the art, for example mixing components in a reducing environment and then introducing the components to an oxidizing environment.

Transport Peptide

A wide variety of molecules (particularly macromolecules such as peptides) intended for cellular uptake were found to be transported poorly across cell membranes. Among the solutions proposed to facilitate cellular uptake have been the use of transporter moieties such as cationic (i.e., positively charged) polymers, peptides and antibody sequences, including polylysine, polyarginine, Antennapedia-derived peptides, HI Tat-derived peptides and the like. (See, for example, U.S. Patents and Publications U.S. Pat. Nos. 4,847,240, 5,652,122, 5,670,617, 5,674,980, 5,747,641, 5,804,604, 5,888,762, 6,316,003, 6,593,292, US2003/0104622, US2003/0199677 and US2003/0206900, all of which are hereby incorporated by reference in their entirety.)

A particular example of a peptide/transporter conjugate is KAI-9803 (SEQ ID NO: 1), which is made up of a δPKC-derived peptide and a HIV Tat-derived transporter peptide. It is currently being developed for human therapeutic use in the treatment of reperfusion injury. As with most pharmaceutical active agents, KAI-9803 is prepared as a pharmaceutical formulation with certain stability, tolerability and bioavailability requirements.

Excipients and Anti-Aggregants

Pharmaceutically acceptable excipients suitable for use as carriers or diluents are well known in the art, and may be used in a variety of formulations. See, e.g., *Remington's Pharmaceutical Sciences*, 18th Edition, A. R. Gennaro, Editor, Mack Publishing Company (1990); *Remington: The Science and Practice of Pharmacy*, 20th Edition, A. R. Gennaro, Editor, Lippincott Williams & Wilkins (2000); *Handbook of Pharmaceutical Excipients*, 3rd Edition, A. H. Kibbe, Editor, American Pharmaceutical Association, and Pharmaceutical Press (2000); and *Handbook of Pharmaceutical Additives*, compiled by Michael and Irene Ash, Gower (1995).

Lyophilized formulations are typically prepared from an active agent dissolved in a pharmaceutically acceptable solvent, optionally including excipients such as bulking agents, solubility enhancers, pH buffers and the like. The solution is subjected to reduced temperatures and pressure to drive off the liquids, leaving a solid cake that can be stored for future use.

The lyophilized formulations of the disclosed invention advantageously include an anti-aggregant, such as a sugar, where such sugars are sufficient to interact with the active agents' hydrophobic and/or positively charged portions to favor their organization with the sugar, rather than aggregation with each other. Suitable anti-aggregant sugars include fructose, lactose, glycerol, mannitol and D-mannose, preferably mannitol.

The transport moieties used to facilitate cellular uptake of peptides (such as the δPKC sequence portion of KAI-9803) share certain attributes (generally being cationic) that contribute to their functionality in vivo, but have been discovered to give rise to the formation of aggregates under lyophilized storage conditions. The modulatory peptides may also possess structural features which facilitate the formation of aggregates. While not wishing to be bound to any particular theory, such aggregation may result from peptide dimerization and a tendency for the peptides to "organize" into aggregates.

The formation of a detrimental level of aggregates interferes with re-dissolution of peptides and peptide conjugates, in turn interfering with administration where the possibility of particulates would be unacceptable for certain routes of administration (e.g., intracoronary). Notwithstanding these drawbacks, the creation of a detrimental level of aggregates in the formulation complicates determining final concentration in that the precise amount of peptide dissolved per unit of liquid. Such a determination cannot be accurately calculated without first determining and then subtracting the weight of undissolved material. Unacceptable levels of aggregation can result in from 0.1 to 50% aggregation of the peptide conjugates. Thus, another aspect of the present invention pertains to the incorporation of an anti-aggregant in lyophilized formulations of peptides or peptide/transporter conjugates. In addition to suppressing the formation of aggregates in the lyophilized product, certain anti-aggregants can enhance the stabilization of the pharmaceutical formulation.

Administration

Parenteral administration is generally characterized by injection, either subcutaneously, intramuscularly, intraperitoneal, intravenously, and in the case of the present invention via intracoronary injection. Injectables can be prepared in conventional forms, either as liquid solutions or suspensions, solid (e.g., dried or lyophilized) forms suitable for reconstitution into solution or suspension in liquid prior to injection, or as emulsions. Generally, suitable excipients include, for example, water, saline, dextrose, glycerol, ethanol or the like. In addition, minor amounts of non-toxic auxiliary substances can be employed, such as wetting or emulsifying agents, pH buffering agents, solubility enhancers, tonicifiers and the like including, for example, sodium acetate, sorbitan monolaurate, triethanolamine oleate, cyclodextrins, etc. Dosage forms for intravenous (IV) administration generally comprise an active agent incorporated into a sterile solution of simple chemicals such as sugars, amino acids or electrolytes, which can be easily carried by the circulatory system and assimilated. Such solutions are typically prepared with saline or buffer. The pH of such IV fluids may vary, and will typically be from 3.5 to 8.0, as known in the art.

The intracoronary injection formulations of the disclosed invention are typically prepared using sodium chloride for injection, USP (preferably 0.9%) for reconstitution of the lyophilized API into solution at concentrations ranging from 0.001 to 2.5 mg/mL, preferably 0.01 to 1.0 mg/mL.

Exemplary Formulations

The pharmaceutical formulations of the disclosed invention preferably include a PKC modulatory peptide, a transport peptide, and an anti-aggregant agent. Typically, the PKC modulatory peptide and the transport peptide are chemically associated with one another. For example, it is preferred that the modulatory peptide and the transport peptide are covalently bonded to one another. In a preferred embodiment, the PKC modulatory peptide and the transport peptide are linked via a disulfide bond.

In a pre-lyophilized embodiment of the invention, the formulation further includes a sufficient amount of a pharmaceutically acceptable solvent (preferably water for injection, USP) to solubilize the foregoing components. A lyophilized embodiment of the invention includes components described above in the form of a solid cake.

The ratio of peptides to anti-aggregant in the disclosed formulations ranges from about 100:1 to about 5:1, preferably from about 80:1 to about 5:1, more preferably from about 80:1 to about 8:1; the actual ratio will depend upon the identity of the components and the concentration desired for the lyophilized and/or reconstituted drug products.

One aspect of the present invention provides a pre-lyophilized formulation for a peptide or peptide/transporter conjugate, as follows:

TABLE 2

| Ingredient | Amount (wt/vol) |
|---|---|
| API | 0.25 to 5.0 mg/mL |
| Anti-aggregant Sugar | 2.0 to 50.0 mg/mL |
| WFI (USP) | q.s. to 100 | and the lyophilized product therefrom.

Another aspect of the preferred peptide or peptide/transporter conjugate formulation can be obtained by lyophilization of the following:

TABLE 3

| Ingredient | Amount (wt/vol) |
|---|---|
| API | 0.1 to 10.0 mg/mL |
| Anti-aggregant Sugar | 5.0 to 40.0 mg/mL |
| WFI (USP) | q.s. to 100 |

A preferred peptide or peptide/transporter conjugate formulation can be obtained by lyophilization of the following:

TABLE 4

| Ingredient | Amount (wt/vol) |
|---|---|
| API | 2.0 to 3.0 mg/mL |
| Anti-aggregant Sugar | 15.0 to 25.0 mg/mL |
| WFI (USP) | q.s. to 100 |

Another preferred peptide or peptide/transporter conjugate formulation can be obtained by lyophilization of the following:

TABLE 5

| Ingredient | Amount (wt/vol) |
|---|---|
| API | 0.5 to 5.0 mg/mL |
| Anti-aggregant Sugar | 10.0 to 30.0 mg/mL |
| WFI (USP) | q.s. to 100 |

Still another preferred peptide or peptide/transporter conjugate formulation can be obtained by lyophilization of the following:

TABLE 6

| Ingredient | Amount (wt/vol %) |
|---|---|
| API | 2.0 to 3.0 mg/mL |
| Anti-aggregant Sugar | 15.0 to 25.0 mg/mL |
| WFI (USP) | q.s. to 100 |

A further preferred peptide/transporter conjugate formulation can be obtained by lyophilization of the following:

TABLE 7

| Ingredient | Amount |
|---|---|
| KAI-9803 | 5.0 mg |
| Mannitol (USP) | 40.0 mg |
| WFI (USP) | 2.0 mL |

Alternatively, aqueous parenteral solutions of KAI-9803 can be prepared substantially free of sugars, at concentrations ranging from about 0.01 to about 10.0 mg/mL, preferably about 0.1 to about 5.0 mg/mL, and most preferably about 0.1 to about 1.0 mg/mL. The pH of such aqueous solutions is adjusted to between about 2.0 and 4.0, preferably between about 2.5 and 3.5.

Methods of Manufacture and Use

The PKC modulatory peptides and the transporter peptides can be synthesized according to conventional (e.g., solid phase) procedures. After activation of the Cys on one of the PKC modulatory and transporter peptides [e.g., using 2,2'-dithiobis(5-nitropyridine) to activate the carrier peptide] the two peptides are coupled, isolated and then purified [e.g., by preparative RP-HPLC using acetonitrile elution in a TEAP buffer (triethylamine and phosphoric acid) giving rise to the purified phosphate salt]. The fractions from the HPLC containing the purified and coupled peptides are then pooled. A pharmaceutically acceptable salt can be exchanged by repeat RP-HPLC eluting with acetonitrile and the desired organic or inorganic acid counter-ion donor (such as acetic acid, hydrochloric acid, tartaric acid and the like, preferably acetic acid). The desired end product is pooled, divided into lyophilization flasks, lyophilized, and transferred to suitable containers for storage prior to formulation (preferably in sealed amber glass containers at reduced temperature, e.g., −20° C.).

The counterion employed during the production of KAI-9803 has a positive effect on solubility and stability. An acetate counterion is used in the preferred embodiment. Other counterions, such as a chloride counterion are also contemplated. And while use of an acetate counterion is a preferred embodiment of the disclosed invention, it is not required.

The pharmaceutical formulations of the present invention can be manufactured according to most accepted practices, for example, as follows:

(a) Appropriate amounts of anti-aggregant, hydrophobic active agent and/or cationic transport moiety are introduced to a suitably sized container (preferably a glass vial) as dry solids.

(B) A pharmaceutically acceptable solvent [e.g., water for injection ("WFI")] is added to the container in an amount sufficient to dissolve the solids and attain a desired concentration.

(C) The solution thus-formed is filtered, aseptically dispensed into a pre-sterilized container, and lyophilized to dryness.

(D) The container is sealed (optionally after first filling the head-space with a non-reactive gas, such as nitrogen) for storage until reconstitution for administration.

It is recommended that such pharmaceutical products be stored at or below room temperature, preferably at about 2-8° C. (more preferably 5° C.), which instructions should be displayed on the container or its attached label, its outer packaging and any package insert included therein.

To reconstitute the lyophilized formulation for administration, the product is first warm to about room temperature before opening. Shortly prior to use, the sealed container is accessed via a needle through the rubber stopper and a pharmaceutically acceptable solvent (such as saline, preferably 9% saline) is added in an amount sufficient to solubilize the lyophilized cake and provide the desired concentration for administration. Such instructions for reconstitution can be provided in a pharmacy manual, on dosing cards, or can be incorporated on the container or its attached label, outer packaging and/or package insert.

Testing

Testing of the pharmaceutical formulations of the present invention can be accomplished by procedures well known in the art, for example, including: determination of active pharmaceutical ingredient identity and concentration by HPLC-UV (measuring absorbance at 206, 220 and/or 280 nm) e.g., before and after lyophilization and reconstitution; determination of water content in lyophilized product; pH of pre-lyophilized solution and reconstituted solution; and appearance of lyophilized cake.

EXAMPLES

The following examples serve to describe more fully the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

Manufacture of KAI-9803 Acetate

A. Peptide Fragment Synthesis

Merrifield resin is pre-swelled in dichloromethane (DCM) for at least 2 hours. The DCM is drained. Transporter and δ-PKC peptides are prepared by solid phase synthesis as follows:
1. deprotection (TFA/DCM),
2. resin washing (2-propanol, methanol, 10% TEA/DCM, methanol and DCM),
3. coupling of the next amino acid residue (t-Boc-AA-OH, using HOBt/HBTU/NMM), and
4. resin washing (methanol and DCM)].

Deprotection and coupling are monitored by performance of a ninhydrin test. After incorporation of the final amino acid residue on each peptide (Cys), the resin peptide is deprotected and washed (steps 1, 2 and 4, above). The peptide-resin bond and side chain protecting groups are cleaved by treatment with HF/anisole and precipitated by ethyl ether.

B. Peptide Fragment Purification and Isolation

Transporter and δ-PKC peptides obtained, e.g., as described in Example IA are subjected to preparative RP-HPLC on a C-18 column, using an acetonitrile gradient in trifluoroacetic acid solution. The acceptance criterion for purity of these intermediate peptides is not less than 90.0%.

C. Coupling

Transporter peptide obtained, e.g., as described in Example IB is activated by contact with 2,2'-dithiobis(5-nitropyridine) and then contacted with the δ-PKC peptide from Example IB to afford the coupled peptide conjugate KAI-9803.

D. Purification, Salt Exchange and Isolation

Crude KAI-9803 obtained, e.g., as described in Example IC is purified by preparative RP-HPLC using an acetonitrile elution in a TEAP buffer (triethylamine and phosphoric acid) on a YMC C-18 column. The fractions resulting from the purification are analyzed by an analytical RP-HPLC in-process method. Those fractions that meet the purity criterion (not less than 95%) are pooled, loaded back onto the same C-18 column and eluted with acetonitrile in an acetic acid buffer to give the corresponding KAI-9803 acetate salt. The thus-purified KAI-9803 acetate salt is pooled, divided into lyophilization flasks and frozen. The frozen flasks are connected to a lyophilizer manifold and the lyophilization is performed. Upon completion of lyophilization, the resulting KAI-9803 acetate powder is weighed, samples are taken for testing, and the remainder transferred into 50 mL amber glass containers. The containers are closed with 20 mm, (grey)butyl, snap-on stoppers, and stored at −20° C.

Example 2

Formulation, Lyophilization, Fill and Finish

KAI-9803 acetate powder (50.0 mg) obtained, e.g., as described in Example ID and mannitol USP (400.0 mg) are dissolved in about 14.0 mL of WFI, followed by the addition of WFI as necessary to total 20 ml (~6 ml) to give a clear, colorless solution. Clarity, color and complete dissolution of solids are confirmed by visual examination. The solution is aseptically filtered through two serial 0.22 μm filters into a class 100 aseptic filling suite. Two mL of the filtered solution are aseptically dispensed into each of ten pre-sterilized 20 mL vials. Each vial is capped with a slotted lyophilization stopper and loaded onto shelves pre-chilled to −50° C. A primary drying cycle is performed at a shelf temperature of 5° C. for not less than 20 hours, followed by a secondary drying step with a shelf temperature of 25° C. for not less than 3 hours. Upon completion of the lyophilization cycle, the vials are stoppered under nitrogen with a partial vacuum and sealed. The stoppered vials are crimped and inspected in a class 10,000 processing suite. The vials are labeled and then moved to 2-8° C. storage under quarantine.

Example 3

Reconstitution of a KAI-9803+Mannitol Formulation

A vial containing a lyophilized pharmaceutical formulation of 5 mg KAI-9803 and 40 mg mannitol (obtained, e.g., as described in Examples 1 and 2) is injected with 20 mL of 0.9% sodium chloride for injection, USP, is added to the vial and the contents are dissolved with gentle swirling to yield a clear solution. To a sterile, empty IV bag is added 18 mL of 0.9% sodium chloride for injection, USP, followed by the addition of 2 mL of KAI-9803 solution (taken from the vial) to yield a total volume of 20 mL of a 0.1 mg/mL solution of KAI-9803 in the IV bag. The solution is stored at room temperature and used within 4 hours of preparation.

Example 4

Stability of Lyophilized KAI-9803 Formulations

Formulations of KAI-9803 are prepared, for example as described in Examples 1 and 2, using mannitol and substituting mannitol with fructose and sucrose as the anti-aggregant sugar for the formulating procedure of Example 2. All of the solutions are visually inspected for clarity, color and complete dissolution of solids, and an aliquot is removed from each. Each aliquot is analyzed for KAI-9803 concentration using HPLC-UV, measuring absorbance at 206 and 280 nm. The remaining solutions are filtered, filled, lyophilized and finished, e.g., as described in Example 2. One set of vials representing each of the formulations is separated for immediate reconstitution and testing (HPLC-UV @ 206/280 nm) to confirm KAI-9803 concentration in the reconstituted product. The remaining vials are divided into groups for storage at reduced temperature (e.g., 2-8° C.), at room temperature, and at elevated temperature (e.g., 35° C.). Sets of vials representing each of the formulations are withdrawn at selected time points (e.g., 1 day, 1 week, 1 month, 3 months, 6 months), are reconstituted, visually inspected and tested for KAI-9803 concentration (HPLC-UV @ 206/280 nm).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

The invention claimed is:

1. A pharmaceutical formulation, comprising: a protein kinase C modulatory peptide chemically coupled to a transport peptide, wherein the modulatory peptide coupled to the transport peptide comprising the amino acid sequence of SEQ ID NO:1; and a sugar serving as an excipient, wherein the sugar and the modulatory peptide coupled to the transport peptide are in a ratio from 100:1 to about 1:1.

2. The formulation of claim 1, wherein the sugar is selected from the group consisting of fructose, lactose, D-mannose and mannitol.

3. The formulation of claim 1, wherein the ratio is from about 80:1 to about 8:1.

4. The formulation of claim 1, wherein the ratio is from about 80:1 to about 5:1.

5. The formulation of claim 1, wherein the formulation is lyophilized.

6. The formulation of claim 1, wherein the ratio is about 5:1.

7. The formulation of claim 1, wherein the formulation is suitable for a parenteral route of administration.

8. The formulation of claim 7, wherein the parenteral route of administration is intracoronary administration.

* * * * *

SEQUENCE LISTING

```
<160> NUMBER OF SEQ ID NOS: 173

<210> SEQ ID NO 1
<211> LENGTH: 23
<212> TYPE: PRT
<213> ORGANISM: Artificial Sequence
<220> FEATURE:
<223> OTHER INFORMATION: PKC modulatory peptide

<400> SEQUENCE: 1

Cys Ser Phe Asn Ser Tyr Glu Leu Gly Ser Leu Cys Tyr Gly Arg Lys
1               5                   10                  15

Lys Arg Arg Gln Arg Arg Arg
            20

<210> SEQ ID NO 2
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 2

Ile Pro Glu Gly Asp Glu Glu Gly
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 3

Gln Leu Val Ile Ala Asn
 1               5

<210> SEQ ID NO 4
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 4

Gly Leu Gly Ala Glu Asn
 1               5

<210> SEQ ID NO 5
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 5

Ala Arg Gly Ala Glu Asn
 1               5

<210> SEQ ID NO 6
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 6

Cys Gly Lys Gly Ala Glu Asn
 1               5

<210> SEQ ID NO 7
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 7

Cys Gly Lys Gly Ala Glu Asn
 1               5

<210> SEQ ID NO 8
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 8

Lys Gln Lys Thr Lys Thr Ile Lys
 1               5

<210> SEQ ID NO 9
```

```
<211> LENGTH: 13
<212> TYPE: PRT
<213> ORGANISM: Artificial Sequence
<220> FEATURE:
<223> OTHER INFORMATION: PKC modulatory peptide

<400> SEQUENCE: 9

Met Asp Pro Asn Gly Leu Ser Asp Pro Tyr Val Lys Leu
 1               5                  10

<210> SEQ ID NO 10
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 10

Ile Pro Asp Pro Lys Ser Glu
 1               5

<210> SEQ ID NO 11
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 11

Ser Leu Asn Pro Glu Trp Asn Glu Thr
 1               5

<210> SEQ ID NO 12
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 12

Val Pro Pro Glu Gly Ser Glu Ala
 1               5

<210> SEQ ID NO 13
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 13

Lys Leu Phe Ile Met Asn
 1               5

<210> SEQ ID NO 14
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 14

Arg Asp Lys Arg Asp Thr Ser
 1               5

<210> SEQ ID NO 15
<211> LENGTH: 9
```

```
<212> TYPE: PRT
<213> ORGANISM: Artificial Sequence
<220> FEATURE:
<223> OTHER INFORMATION: PKC modulatory peptide

<400> SEQUENCE: 15

Cys Ala Arg Asp Lys Arg Asp Thr Ser
1               5

<210> SEQ ID NO 16
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 16

Gly Arg Asp Lys Arg Asp Thr Ser
1               5

<210> SEQ ID NO 17
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 17

Ala Arg Asp Lys Arg Asp Thr Ser
1               5

<210> SEQ ID NO 18
<211> LENGTH: 12
<212> TYPE: PRT
<213> ORGANISM: Artificial Sequence
<220> FEATURE:
<223> OTHER INFORMATION: PKC modulatory peptide

<400> SEQUENCE: 18

Ala Arg Asp Lys Arg Asp Thr Ser Asn Phe Asp Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: PKC modulatory peptide

<400> SEQUENCE: 19

Ala Gly Phe Ser Tyr Thr Asn Pro Glu Phe Val Ile Asn Val
1               5                   10

<210> SEQ ID NO 20
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 20

Gln Glu Val Ile Arg Asn
1               5

<210> SEQ ID NO 21
<211> LENGTH: 6
<212> TYPE: PRT
```

```
<213> ORGANISM: Artificial Sequence
<220> FEATURE:
<223> OTHER INFORMATION: PKC modulatory peptide

<400> SEQUENCE: 21

Cys Gly Arg Asn Ala Glu
 1               5

<210> SEQ ID NO 22
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 22

Ala Cys Gly Arg Asn Ala Glu
 1               5

<210> SEQ ID NO 23
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 23

Ala Cys Gly Lys Asn Ala Glu
 1               5

<210> SEQ ID NO 24
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 24

Lys Ala Cys Gly Arg Asn Ala Glu
 1               5

<210> SEQ ID NO 25
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 25

Cys Gly Arg Asn Ala Glu Asn
 1               5

<210> SEQ ID NO 26
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 26

Ala Cys Gly Arg Asn Ala Glu
 1               5

<210> SEQ ID NO 27
<211> LENGTH: 14
<212> TYPE: PRT
<213> ORGANISM: Artificial Sequence
```

```
<220> FEATURE:
<223> OTHER INFORMATION: PKC modulatory peptide

<400> SEQUENCE: 27

Ser Phe Val Asn Ser Glu Phe Leu Lys Pro Glu Val Leu Ser
 1               5                  10

<210> SEQ ID NO 28
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 28

Val Ala Asp Ala Asp Asn Cys Ser
 1               5

<210> SEQ ID NO 29
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 29

Gly Arg Ser Gly Glu Asn
 1               5

<210> SEQ ID NO 30
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 30

Gly Leu Ser Gly Glu Asn
 1               5

<210> SEQ ID NO 31
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 31

Arg Leu Val Leu Ala Ser
 1               5

<210> SEQ ID NO 32
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 32

Pro Cys Gly Arg Ser Gly Glu Asn
 1               5

<210> SEQ ID NO 33
<211> LENGTH: 11
<212> TYPE: PRT
<213> ORGANISM: Artificial Sequence
<220> FEATURE:
```

```
<223> OTHER INFORMATION: PKC modulatory peptide

<400> SEQUENCE: 33

Cys Ser Phe Asn Ser Tyr Glu Leu Gly Ser Leu
 1               5                  10

<210> SEQ ID NO 34
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 34

Ser Phe Asn Ser Tyr Glu Leu Gly Ser Leu
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 35

Thr Phe Asn Ser Tyr Glu Leu Gly Ser Leu
 1               5                  10

<210> SEQ ID NO 36
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 36

Ala Phe Asn Ser Asn Tyr Glu Leu Gly Ser Leu
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 37

Ser Phe Asn Ser Tyr Glu Leu Gly Thr Leu
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 38

Ser Thr Asn Ser Tyr Glu Leu Gly Ser Leu
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: PKC modulatory peptide
```

```
<400> SEQUENCE: 39

Ser Phe Asn Ser Phe Glu Leu Gly Ser Leu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 40

Ser Asn Ser Tyr Asp Leu Gly Ser Leu
1               5

<210> SEQ ID NO 41
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 41

Ser Phe Asn Ser Tyr Glu Leu Pro Ser Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 42

Thr Phe Asn Ser Tyr Glu Leu Gly Thr Leu
1               5                   10

<210> SEQ ID NO 43
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 43

Ser Phe Asn Ser Tyr Glu Ile Gly Ser Val
1               5                   10

<210> SEQ ID NO 44
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 44

Ser Phe Asn Ser Tyr Glu Val Gly Ser Ile
1               5                   10

<210> SEQ ID NO 45
<211> LENGTH: 10
<212> TYPE: PRT
<213> ORGANISM: Artificial Sequence
<220> FEATURE:
<223> OTHER INFORMATION: PKC modulatory peptide
```

```
<400> SEQUENCE: 45

Ser Phe Asn Ser Tyr Glu Leu Gly Ser Val
1               5                   10

<210> SEQ ID NO 46
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 46

Ser Phe Asn Ser Tyr Glu Leu Gly Ser Ile
1               5                   10

<210> SEQ ID NO 47
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 47

Ser Phe Asn Ser Tyr Glu Ile Gly Ser Leu
1               5                   10

<210> SEQ ID NO 48
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 48

Ser Phe Asn Ser Tyr Glu Val Gly Ser Leu
1               5                   10

<210> SEQ ID NO 49
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 49

Ala Phe Asn Ser Tyr Glu Leu Gly Ser Leu
1               5                   10

<210> SEQ ID NO 50
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 50

Tyr Asp Leu Gly Ser Leu
1               5

<210> SEQ ID NO 51
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 51
```

Phe Asp Leu Gly Ser Leu
1               5

<210> SEQ ID NO 52
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 52

Tyr Asp Ile Gly Ser Leu
1               5

<210> SEQ ID NO 53
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 53

Tyr Asp Val Gly Ser Leu
1               5

<210> SEQ ID NO 54
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 54

Tyr Asp Leu Pro Ser Leu
1               5

<210> SEQ ID NO 55
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 55

Tyr Asp Leu Gly Leu Leu
1               5

<210> SEQ ID NO 56
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 56

Tyr Asp Leu Gly Ser Ile
1               5

<210> SEQ ID NO 57
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 57

Tyr Asp Leu Gly Ser Val
1               5

<210> SEQ ID NO 58
<211> LENGTH: 4
<212> TYPE: PRT
<213> ORGANISM: Artificial Sequence
<220> FEATURE:
<223> OTHER INFORMATION: PKC modulatory peptide

<400> SEQUENCE: 58

Ile Gly Ser Leu
1

<210> SEQ ID NO 59
<211> LENGTH: 4
<212> TYPE: PRT
<213> ORGANISM: Artificial Sequence
<220> FEATURE:
<223> OTHER INFORMATION: PKC modulatory peptide

<400> SEQUENCE: 59

Val Gly Ser Leu
1

<210> SEQ ID NO 60
<211> LENGTH: 4
<212> TYPE: PRT
<213> ORGANISM: Artificial Sequence
<220> FEATURE:
<223> OTHER INFORMATION: PKC modulatory peptide

<400> SEQUENCE: 60

Leu Pro Ser Leu
1

<210> SEQ ID NO 61
<211> LENGTH: 4
<212> TYPE: PRT
<213> ORGANISM: Artificial Sequence
<220> FEATURE:
<223> OTHER INFORMATION: PKC modulatory peptide

<400> SEQUENCE: 61

Leu Gly Leu Leu
1

<210> SEQ ID NO 62
<211> LENGTH: 4
<212> TYPE: PRT
<213> ORGANISM: Artificial Sequence
<220> FEATURE:
<223> OTHER INFORMATION: PKC modulatory peptide

<400> SEQUENCE: 62

Leu Gly Ser Ile
1

<210> SEQ ID NO 63
<211> LENGTH: 4
<212> TYPE: PRT
<213> ORGANISM: Artificial Sequence
<220> FEATURE:
<223> OTHER INFORMATION: PKC modulatory peptide

<400> SEQUENCE: 63

Leu Gly Ser Val

```
<210> SEQ ID NO 64
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 64

Ala Leu Ser Thr Glu Arg Gly Lys Thr Leu Val
 1               5                   10

<210> SEQ ID NO 65
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 65

Ala Leu Ser Thr Asp Arg Gly Lys Thr Leu Val
 1               5                   10

<210> SEQ ID NO 66
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 66

Ala Leu Thr Ser Asp Arg Gly Lys Thr Leu Val
 1               5                   10

<210> SEQ ID NO 67
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 67

Ala Leu Thr Thr Asp Arg Gly Lys Ser Leu Val
 1               5                   10

<210> SEQ ID NO 68
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 68

Ala Leu Thr Thr Asp Arg Pro Lys Thr Leu Val
 1               5                   10

<210> SEQ ID NO 69
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 69

Ala Leu Thr Thr Asp Arg Gly Arg Thr Leu Val
 1               5                   10
```

```
<210> SEQ ID NO 70
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 70

Ala Leu Thr Thr Asp Lys Gly Lys Thr Leu Val
 1               5                  10

<210> SEQ ID NO 71
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 71

Ala Leu Thr Thr Asp Lys Gly Lys Thr Leu Val
 1               5                  10

<210> SEQ ID NO 72
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 72

Val Leu Met Arg Ala Ala Glu Glu Pro Val
 1               5                  10

<210> SEQ ID NO 73
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 73

Gln Ser Met Arg Ser Glu Asp Glu Ala Lys
 1               5                  10

<210> SEQ ID NO 74
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 74

Gln Gly Phe Glu Lys Lys Thr Gly Val
 1               5

<210> SEQ ID NO 75
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 75

Asp Asn Asn Gly Thr Tyr Gly Lys Ile
 1               5
```

```
<210> SEQ ID NO 76
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 76

Lys Asn Leu Ile Asp Ser
 1               5

<210> SEQ ID NO 77
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 77

Val Lys Ser Pro Arg Asp Tyr Ser
 1               5

<210> SEQ ID NO 78
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 78

Val Lys Ser Pro Cys Arg Asp Tyr Ser
 1               5

<210> SEQ ID NO 79
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 79

Ile Lys Ser Pro Arg Leu Tyr Ser
 1               5

<210> SEQ ID NO 80
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 80

Lys Asn Leu Ile Asp Ser
 1               5

<210> SEQ ID NO 81
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 81

Pro Lys Val Lys Ser Pro Arg Asp Tyr Ser Asn
 1               5                  10
```

<210> SEQ ID NO 82
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 82

Asn Gly Leu Leu Lys Ile Lys
 1               5

<210> SEQ ID NO 83
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 83

Glu Ala Val Ser Leu Lys Pro Thr
 1               5

<210> SEQ ID NO 84
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 84

Leu Ala Val Phe His Asp Ala Pro Ile Gly Tyr
 1               5                   10

<210> SEQ ID NO 85
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 85

Asp Asp Phe Val Ala Asn Cys Thr Ile
 1               5

<210> SEQ ID NO 86
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 86

Trp Ile Asp Leu Glu Pro Glu Gly Arg Val
 1               5                   10

<210> SEQ ID NO 87
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 87

His Ala Val Gly Pro Arg Pro Gln Thr Phe
 1               5                   10

<210> SEQ ID NO 88

```
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 88

Asn Gly Ser Arg His Phe Glu Asp
 1               5

<210> SEQ ID NO 89
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 89

His Asp Ala Pro Ile Gly Asp Tyr
 1               5

<210> SEQ ID NO 90
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 90

His Asp Ala Pro Ile Gly
 1               5

<210> SEQ ID NO 91
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 91

His Asp Ala Ala Ile Gly Tyr Asp
 1               5

<210> SEQ ID NO 92
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 92

His Asp Ala Pro Ile Pro Tyr Asp
 1               5

<210> SEQ ID NO 93
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 93

His Asn Ala Pro Ile Gly Tyr Asp
 1               5

<210> SEQ ID NO 94
<211> LENGTH: 8
```

```
<212> TYPE: PRT
<213> ORGANISM: Artificial Sequence
<220> FEATURE:
<223> OTHER INFORMATION: PKC modulatory peptide

<400> SEQUENCE: 94

His Ala Ala Pro Ile Gly Tyr Asp
 1               5

<210> SEQ ID NO 95
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 95

Ala Asp Ala Pro Ile Gly Tyr Asp
 1               5

<210> SEQ ID NO 96
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 96

His Asp Ala Pro Ala Gly Tyr Asp
 1               5

<210> SEQ ID NO 97
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 97

His Asp Ala Pro Ile Gly Ala Asp
 1               5

<210> SEQ ID NO 98
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 98

His Asp Ala Pro Ile Ala Tyr Asp
 1               5

<210> SEQ ID NO 99
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 99

His Asp Ala Pro Ile Gly Tyr Ala
 1               5

<210> SEQ ID NO 100
<211> LENGTH: 9
<212> TYPE: PRT
```

```
<213> ORGANISM: Artificial Sequence
<220> FEATURE:
<223> OTHER INFORMATION: PKC modulatory peptide

<400> SEQUENCE: 100

Ser Ser Pro Ser Glu Glu Asp Arg Ser
 1               5

<210> SEQ ID NO 101
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 101

Pro Cys Asp Gln Glu Ile Lys Glu
 1               5

<210> SEQ ID NO 102
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 102

Glu Asn Asn Ile Arg Lys Ala Leu Ser
 1               5

<210> SEQ ID NO 103
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 103

Gly Glu Val Arg Gln Gly Gln Ala
 1               5

<210> SEQ ID NO 104
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 104

Glu Ala Ile Val Lys Gln
 1               5

<210> SEQ ID NO 105
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 105

Ile Lys Thr Lys Arg Asp Val
 1               5

<210> SEQ ID NO 106
<211> LENGTH: 7
<212> TYPE: PRT
<213> ORGANISM: Artificial Sequence
```

```
<220> FEATURE:
<223> OTHER INFORMATION: PKC modulatory peptide

<400> SEQUENCE: 106

Ile Lys Thr Lys Arg Leu Ile
1               5

<210> SEQ ID NO 107
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 107

Cys Glu Ala Ile Val Lys Gln
1               5

<210> SEQ ID NO 108
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 108

Thr Lys Arg Asp Val Asn Asn Phe Asp Gln
1               5                   10

<210> SEQ ID NO 109
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 109

Val Arg Leu Lys Ala His Tyr
1               5

<210> SEQ ID NO 110
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 110

Val Asp Ser Glu Gly Asp
1               5

<210> SEQ ID NO 111
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 111

Val Phe Pro Ser Ile Pro Glu Gln
1               5

<210> SEQ ID NO 112
<211> LENGTH: 15
<212> TYPE: PRT
<213> ORGANISM: Artificial Sequence
<220> FEATURE:
```

<223> OTHER INFORMATION: PKC modulatory peptide

<400> SEQUENCE: 112

Ser Gln Glu Pro Pro Val Asp Lys Asn Glu Asp Ala Asp Leu
1               5                   10                  15

<210> SEQ ID NO 113
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 113

Ile Lys Asp Asp Ser Glu Asp
1               5

<210> SEQ ID NO 114
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 114

Pro Val Ile Asp Gly Met Asp Gly Ile
1               5

<210> SEQ ID NO 115
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 115

Glu Asp Ala Ile Lys Arg
1               5

<210> SEQ ID NO 116
<211> LENGTH: 5
<212> TYPE: PRT
<213> ORGANISM: Artificial Sequence
<220> FEATURE:
<223> OTHER INFORMATION: PKC modulatory peptide

<400> SEQUENCE: 116

Glu Asp Ala Ile Arg
1               5

<210> SEQ ID NO 117
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 117

Ile Thr Asp Asp Tyr Gly Leu Asp
1               5

<210> SEQ ID NO 118
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 118

Ile Thr Asp Asp Tyr Gly Asp Leu
1               5

<210> SEQ ID NO 119
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 119

Asp Asp Tyr Gly Leu Asp Asn
1               5

<210> SEQ ID NO 120
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 120

Asn Gly Tyr Leu Arg Val Arg
1               5

<210> SEQ ID NO 121
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 121

Glu Ala Val Gly Leu Gln Pro Thr
1               5

<210> SEQ ID NO 122
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 122

Leu Ala Val Phe His Glu Thr Pro Leu Gly Tyr
1               5                   10

<210> SEQ ID NO 123
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 123

Asp Phe Val Ala Asn Cys Thr Leu
1               5

<210> SEQ ID NO 124
<211> LENGTH: 10
<212> TYPE: PRT
<213> ORGANISM: Artificial Sequence
<220> FEATURE:
<223> OTHER INFORMATION: PKC modulatory peptide

```
<400> SEQUENCE: 124

Trp Val Asp Leu Glu Pro Glu Gly Lys Val
 1               5                  10

<210> SEQ ID NO 125
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 125

His Ser Leu Phe Lys Lys Gly His
 1               5

<210> SEQ ID NO 126
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 126

Thr Gly Ala Ser Asp Thr Phe Glu Gly
 1               5

<210> SEQ ID NO 127
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 127

Glu Gly His Leu Pro Met
 1               5

<210> SEQ ID NO 128
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 128

Glu Gly His Asp Pro Met
 1               5

<210> SEQ ID NO 129
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 129

Ile Lys Ser Arg Glu Asp Val Ser
 1               5

<210> SEQ ID NO 130
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 130
```

```
Val Arg Ser Arg Glu Asp Val Ser
 1               5
```

<210> SEQ ID NO 131
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 131

```
Pro Arg Ile Lys Ser Arg Glu Asp Val
 1               5
```

<210> SEQ ID NO 132
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 132

```
His Gln Val Arg Val Lys Ala Tyr Tyr Arg
 1               5                  10
```

<210> SEQ ID NO 133
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 133

```
Tyr Glu Leu Asn Lys Asp Ser Glu Leu Leu Ile
 1               5                  10
```

<210> SEQ ID NO 134
<211> LENGTH: 15
<212> TYPE: PRT
<213> ORGANISM: Artificial Sequence
<220> FEATURE:
<223> OTHER INFORMATION: PKC modulatory peptide

<400> SEQUENCE: 134

```
Met Asp Gln Ser Ser Met His Ser Asp His Ala Gln Thr Val Ile
 1               5                  10                  15
```

<210> SEQ ID NO 135
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 135

```
Leu Asp Gln Val Gly Glu Glu
 1               5
```

<210> SEQ ID NO 136
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 136

```
Glu Ala Met Asn Thr Arg Glu Ser Gly
1               5
```

<210> SEQ ID NO 137
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 137

```
Asp Asp Ile Val Arg Lys
1               5
```

<210> SEQ ID NO 138
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 138

```
Val Lys Leu Cys Asp Phe Gly Phe
1               5
```

<210> SEQ ID NO 139
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 139

```
Ile Arg Leu Cys Asp Phe Ala Phe
1               5
```

<210> SEQ ID NO 140
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 140

```
Gln Val Lys Leu Cys Asp Phe Gly Phe Ala
1               5                   10
```

<210> SEQ ID NO 141
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 141

```
Met Ser Val Pro Pro Leu Leu Arg Pro
1               5
```

<210> SEQ ID NO 142
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 142

```
Lys Phe Pro Glu Cys Gly Phe Tyr Gly Leu Tyr
```

<210> SEQ ID NO 143
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 143

Asp Pro Asp Ala Asp Gln Glu Asp Ser
1               5

<210> SEQ ID NO 144
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 144

Ser Lys Asp Thr Leu Arg Lys Arg His
1               5

<210> SEQ ID NO 145
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 145

Ile Thr Leu Phe Gln Asn Asp Thr Gly
1               5

<210> SEQ ID NO 146
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 146

Gly Ser Asn Ser His Lys Asp Ile Ser
1               5

<210> SEQ ID NO 147
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 147

Ser Asp Ser Pro Glu Ala
1               5

<210> SEQ ID NO 148
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 148

Gly Leu Ser Asn Phe Asp Cys Gly
1               5

-continued

```
<210> SEQ ID NO 149
<211> LENGTH: 11
<212> TYPE: PRT
<213> ORGANISM: Artificial Sequence
<220> FEATURE:
<223> OTHER INFORMATION: PKC modulatory peptide

<400> SEQUENCE: 149

Tyr Val Glu Ser Glu Asn Gly Gln Met Tyr Ile
 1               5                  10

<210> SEQ ID NO 150
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 150

Ile Val Lys Gly Lys Asn Val Asp Leu Ile
 1               5                  10

<210> SEQ ID NO 151
<211> LENGTH: 10
<212> TYPE: PRT
<213> ORGANISM: Artificial Sequence
<220> FEATURE:
<223> OTHER INFORMATION: PKC modulatory peptide

<400> SEQUENCE: 151

Asp Met Asn Glu Phe Glu Thr Glu Gly Phe
 1               5                  10

<210> SEQ ID NO 152
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 152

Cys Ser Ile Lys Asn Glu Ala Arg Leu
 1               5

<210> SEQ ID NO 153
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 153

Gly Lys Arg Glu Pro Gln Gly Ile Ser
 1               5

<210> SEQ ID NO 154
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 154

Asp Glu Val Asp Lys Met Cys His Leu
 1               5
```

```
<210> SEQ ID NO 155
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 155

Arg Ala Leu Ile Asn Ser
 1               5

<210> SEQ ID NO 156
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 156

Val Lys Ser Pro Phe Asp Cys Ser
 1               5

<210> SEQ ID NO 157
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 157

Val Arg Ser Pro Phe Asp Cys Ser
 1               5

<210> SEQ ID NO 158
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 158

Asp Arg Ala Leu Ile Asn Ser
 1               5

<210> SEQ ID NO 159
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 159

Ile Ser Gly Glu Phe Gly Leu Asp
 1               5

<210> SEQ ID NO 160
<211> LENGTH: 8
<212> TYPE: PRT
<213> ORGANISM: Artificial Sequence
<220> FEATURE:
<223> OTHER INFORMATION: PKC modulatory peptide

<400> SEQUENCE: 160

Cys Ser Gly Glu Phe Gly Leu Asp
 1               5
```

```
<210> SEQ ID NO 161
<211> LENGTH: 7
<212> TYPE: PRT
<213> ORGANISM: Artificial Sequence
<220> FEATURE:
<223> OTHER INFORMATION: PKC modulatory peptide

<400> SEQUENCE: 161

Asp Asp Asp Ile Val Arg Lys
 1               5

<210> SEQ ID NO 162
<211> LENGTH: 6
<212> TYPE: PRT
<213> ORGANISM: Artificial Sequence
<220> FEATURE:
<223> OTHER INFORMATION: PKC modulatory peptide

<400> SEQUENCE: 162

Asp Asp Ile Val Arg Lys
 1               5

<210> SEQ ID NO 163
<211> LENGTH: 9
<212> TYPE: PRT
<213> ORGANISM: Artificial Sequence
<220> FEATURE:
<223> OTHER INFORMATION: PKC modulatory peptide

<400> SEQUENCE: 163

Ala Phe Asn Ser Tyr Glu Leu Gly Ser
 1               5

<210> SEQ ID NO 164
<211> LENGTH: 672
<212> TYPE: PRT
<213> ORGANISM: Homo sapiens

<400> SEQUENCE: 164

Met Ala Asp Val Phe Pro Gly Asn Asp Ser Thr Ala Ser Gln Asp Val
 1               5                   10                  15

Ala Asn Arg Phe Ala Arg Lys Gly Ala Leu Arg Gln Lys Asn Val His
                20                  25                  30

Glu Val Lys Asp His Lys Phe Ile Ala Arg Phe Phe Lys Gln Pro Thr
            35                  40                  45

Phe Cys Ser His Cys Thr Asp Phe Ile Trp Gly Phe Gly Lys Gln Gly
        50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Asp Met Asn Val His Lys Gln Cys Val
    130                 135                 140

Ile Asn Val Pro Ser Leu Cys Gly Met Asp His Thr Glu Lys Arg Gly
145                 150                 155                 160

Arg Ile Tyr Leu Lys Ala Glu Val Ala Asp Glu Lys Leu His Val Thr
                165                 170                 175
```

```
Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
        195                 200                 205

Lys Gln Lys Thr Lys Thr Ile Arg Ser Thr Leu Asn Pro Gln Trp Asn
    210                 215                 220

Glu Ser Phe Thr Phe Lys Leu Lys Pro Ser Asp Lys Asp Arg Arg Leu
225                 230                 235                 240

Ser Val Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
            260                 265                 270

Gly Trp Tyr Lys Leu Leu Asn Gln Glu Glu Gly Glu Tyr Tyr Asn Val
        275                 280                 285

Pro Ile Pro Glu Gly Asp Glu Glu Gly Asn Met Glu Leu Arg Gln Lys
    290                 295                 300

Phe Glu Lys Ala Lys Leu Gly Pro Ala Gly Asn Lys Val Ile Ser Pro
305                 310                 315                 320

Ser Glu Asp Arg Lys Gln Pro Ser Asn Asn Leu Asp Arg Val Lys Leu
                325                 330                 335

Thr Asp Phe Asn Phe Leu Met Val Leu Gly Lys Gly Ser Phe Gly Lys
            340                 345                 350

Val Met Leu Ala Asp Arg Lys Gly Thr Glu Glu Leu Tyr Ala Ile Lys
        355                 360                 365

Ile Leu Lys Lys Asp Val Val Ile Gln Asp Asp Asp Val Glu Cys Thr
    370                 375                 380

Met Val Glu Lys Arg Val Leu Ala Leu Leu Asp Lys Pro Pro Phe Leu
385                 390                 395                 400

Thr Gln Leu His Ser Cys Phe Gln Thr Val Asp Arg Leu Tyr Phe Val
                405                 410                 415

Met Glu Tyr Val Asn Gly Gly Asp Leu Met Tyr His Ile Gln Gln Val
            420                 425                 430

Gly Lys Phe Lys Glu Pro Gln Ala Val Phe Tyr Ala Ala Glu Ile Ser
        435                 440                 445

Ile Gly Leu Phe Phe Leu His Lys Arg Gly Ile Ile Tyr Arg Asp Leu
    450                 455                 460

Lys Leu Asp Asn Val Met Leu Asp Ser Glu Gly His Ile Lys Ile Ala
465                 470                 475                 480

Asp Phe Gly Met Cys Lys Glu His Met Met Asp Gly Val Thr Thr Arg
                485                 490                 495

Thr Phe Cys Gly Thr Pro Asp Tyr Ile Ala Pro Glu Ile Ile Ala Tyr
            500                 505                 510

Gln Pro Tyr Gly Lys Ser Val Asp Trp Trp Ala Tyr Gly Val Leu Leu
        515                 520                 525

Tyr Glu Met Leu Ala Gly Gln Pro Pro Phe Asp Gly Glu Asp Glu Asp
    530                 535                 540

Glu Leu Phe Gln Ser Ile Met Glu His Asn Val Ser Tyr Pro Lys Ser
545                 550                 555                 560

Leu Ser Lys Glu Ala Val Ser Ile Cys Lys Gly Leu Met Thr Lys His
                565                 570                 575

Pro Ala Lys Arg Leu Gly Cys Gly Pro Glu Gly Glu Arg Asp Val Arg
            580                 585                 590

Glu His Ala Phe Phe Arg Arg Ile Asp Trp Glu Lys Leu Glu Asn Arg
```

```
                    595                 600                 605
Glu Ile Gln Pro Pro Phe Lys Pro Lys Val Cys Gly Lys Gly Ala Glu
    610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
                645                 650                 655

Ser Tyr Val Asn Pro Gln Phe Val His Pro Ile Leu Gln Ser Ala Val
                660                 665                 670

<210> SEQ ID NO 165
<211> LENGTH: 671
<212> TYPE: PRT
<213> ORGANISM: Homo sapiens

<400> SEQUENCE: 165

Met Ala Asp Pro Ala Gly Pro Pro Ser Glu Gly Glu Glu Ser
  1               5                  10                  15

Thr Val Arg Phe Ala Arg Lys Gly Ala Leu Arg Gln Lys Asn Val His
                 20                  25                  30

Glu Val Lys Asn His Lys Phe Thr Ala Arg Phe Phe Lys Gln Pro Thr
             35                  40                  45

Phe Cys Ser His Cys Thr Asp Phe Ile Trp Gly Phe Gly Lys Gln Gly
 50                  55                  60

Phe Gln Cys Gln Val Cys Cys Phe Val Val His Lys Arg Cys His Glu
 65                  70                  75                  80

Phe Val Thr Phe Ser Cys Pro Gly Ala Asp Lys Gly Pro Ala Ser Asp
                 85                  90                  95

Asp Pro Arg Ser Lys His Lys Phe Lys Ile His Thr Tyr Ser Ser Pro
                100                 105                 110

Thr Phe Cys Asp His Cys Gly Ser Leu Leu Tyr Gly Leu Ile His Gln
                115                 120                 125

Gly Met Lys Cys Asp Thr Cys Met Met Asn Val His Lys Arg Cys Val
    130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                165                 170                 175

Val Arg Asp Ala Lys Asn Leu Val Pro Met Asp Pro Asn Gly Leu Ser
                180                 185                 190

Asp Pro Tyr Val Lys Leu Lys Leu Ile Pro Asp Pro Lys Ser Glu Ser
                195                 200                 205

Lys Gln Lys Thr Lys Thr Ile Lys Cys Ser Leu Asn Pro Glu Trp Asn
    210                 215                 220

Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                245                 250                 255

Gly Ser Leu Ser Phe Gly Ile Ser Glu Leu Gln Lys Ala Ser Val Asp
                260                 265                 270

Gly Trp Phe Lys Leu Leu Ser Gln Glu Glu Gly Glu Tyr Phe Asn Val
    275                 280                 285

Pro Val Pro Pro Glu Gly Ser Glu Ala Asn Glu Glu Leu Arg Gln Lys
290                 295                 300
```

```
Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
            325                 330                 335

Met Lys Leu Thr Asp Phe Asn Phe Leu Met Val Leu Gly Lys Gly Ser
            340                 345                 350

Phe Gly Lys Val Met Leu Ser Glu Arg Lys Gly Thr Asp Glu Leu Tyr
        355                 360                 365

Ala Val Lys Ile Leu Lys Lys Asp Val Val Ile Gln Asp Asp Asp Val
    370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
            405                 410                 415

Tyr Phe Val Met Glu Tyr Val Asn Gly Gly Asp Leu Met Tyr His Ile
            420                 425                 430

Gln Gln Val Gly Arg Phe Lys Glu Pro His Ala Val Phe Tyr Ala Ala
        435                 440                 445

Glu Ile Ala Ile Gly Leu Phe Phe Leu Gln Ser Lys Gly Ile Ile Tyr
    450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
            485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
        515                 520                 525

Val Leu Leu Tyr Glu Met Leu Ala Gly Gln Ala Pro Phe Glu Gly Glu
    530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
            565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
        595                 600                 605

Glu Arg Lys Glu Ile Gln Pro Pro Tyr Lys Pro Lys Ala Arg Asp Lys
    610                 615                 620

Arg Asp Thr Ser Asn Phe Asp Lys Glu Phe Thr Arg Gln Pro Val Glu
625                 630                 635                 640

Leu Thr Pro Thr Asp Lys Leu Phe Ile Met Asn Leu Asp Gln Asn Glu
            645                 650                 655

Phe Ala Gly Phe Ser Tyr Thr Asn Pro Glu Phe Val Ile Asn Val
            660                 665                 670
```

<210> SEQ ID NO 166
<211> LENGTH: 673
<212> TYPE: PRT
<213> ORGANISM: Homo sapiens

<400> SEQUENCE: 166

```
Met Ala Asp Pro Ala Ala Gly Pro Pro Pro Ser Glu Gly Glu Glu Ser
1               5                   10                  15
```

-continued

Thr Val Arg Phe Ala Arg Lys Gly Ala Leu Arg Gln Lys Asn Val His
            20                  25                  30

Glu Val Lys Asn His Lys Phe Thr Ala Arg Phe Phe Lys Gln Pro Thr
            35                  40                  45

Phe Cys Ser His Cys Thr Asp Phe Ile Trp Gly Phe Gly Lys Gln Gly
        50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Ala Ser Asp
                    85                  90                  95

Asp Pro Arg Ser Lys His Lys Phe Lys Ile His Thr Tyr Ser Ser Pro
            100                 105                 110

Thr Phe Cys Asp His Cys Gly Ser Leu Leu Tyr Gly Leu Ile His Gln
            115                 120                 125

Gly Met Lys Cys Asp Thr Cys Met Met Asn Val His Lys Arg Cys Val
    130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                165                 170                 175

Val Arg Asp Ala Lys Asn Leu Val Pro Met Asp Pro Asn Gly Leu Ser
            180                 185                 190

Asp Pro Tyr Val Lys Leu Lys Leu Ile Pro Asp Pro Lys Ser Glu Ser
            195                 200                 205

Lys Gln Lys Thr Lys Thr Ile Lys Cys Ser Leu Asn Pro Glu Trp Asn
    210                 215                 220

Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                245                 250                 255

Gly Ser Leu Ser Phe Gly Ile Ser Glu Leu Gln Lys Ala Ser Val Asp
            260                 265                 270

Gly Trp Phe Lys Leu Leu Ser Gln Glu Glu Gly Glu Tyr Phe Asn Val
            275                 280                 285

Pro Val Pro Pro Glu Gly Ser Glu Ala Asn Glu Glu Leu Arg Gln Lys
            290                 295                 300

Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
                325                 330                 335

Met Lys Leu Thr Asp Phe Asn Phe Leu Met Val Leu Gly Lys Gly Ser
            340                 345                 350

Phe Gly Lys Val Met Leu Ser Glu Arg Lys Gly Thr Asp Glu Leu Tyr
            355                 360                 365

Ala Val Lys Ile Leu Lys Lys Asp Val Val Ile Gln Asp Asp Asp Val
        370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
                405                 410                 415

Tyr Phe Val Met Glu Tyr Val Asn Gly Gly Asp Leu Met Tyr His Ile
            420                 425                 430

```
Gln Gln Val Gly Arg Phe Lys Glu Pro His Ala Val Phe Tyr Ala Ala
        435                 440                 445
Glu Ile Ala Ile Gly Leu Phe Phe Leu Gln Ser Lys Gly Ile Ile Tyr
    450                 455                 460
Arg Asp Leu Lys Leu Asp Asn Val Met Leu Asp Ser Glu Gly His Ile
465                 470                 475                 480
Lys Ile Ala Asp Phe Gly Met Cys Lys Glu Asn Ile Trp Asp Gly Val
                485                 490                 495
Thr Thr Lys Thr Phe Cys Gly Thr Pro Asp Tyr Ile Ala Pro Glu Ile
            500                 505                 510
Ile Ala Tyr Gln Pro Tyr Gly Lys Ser Val Asp Trp Trp Ala Phe Gly
        515                 520                 525
Val Leu Leu Tyr Glu Met Leu Ala Gly Gln Ala Pro Phe Glu Gly Glu
    530                 535                 540
Asp Glu Asp Glu Leu Phe Gln Ser Ile Met Glu His Asn Val Ala Tyr
545                 550                 555                 560
Pro Lys Ser Met Ser Lys Glu Ala Val Ala Ile Cys Lys Gly Leu Met
                565                 570                 575
Thr Lys His Pro Gly Lys Arg Leu Gly Cys Gly Pro Glu Gly Glu Arg
            580                 585                 590
Asp Ile Lys Glu His Ala Phe Phe Arg Tyr Ile Asp Trp Glu Lys Leu
        595                 600                 605
Glu Arg Lys Glu Ile Gln Pro Pro Tyr Lys Pro Lys Ala Cys Gly Arg
    610                 615                 620
Asn Ala Glu Asn Phe Asp Arg Phe Phe Thr Arg His Pro Pro Val Leu
625                 630                 635                 640
Thr Pro Pro Asp Gln Glu Val Ile Arg Asn Ile Asp Gln Ser Glu Phe
                645                 650                 655
Glu Gly Phe Ser Phe Val Asn Ser Glu Phe Leu Lys Pro Glu Val Lys
            660                 665                 670
Ser

<210> SEQ ID NO 167
<211> LENGTH: 697
<212> TYPE: PRT
<213> ORGANISM: Homo sapiens

<400> SEQUENCE: 167

Met Ala Gly Leu Gly Pro Gly Val Gly Asp Ser Glu Gly Gly Pro Arg
1               5                   10                  15
Pro Leu Phe Cys Arg Lys Gly Ala Leu Arg Gln Lys Val Val His Glu
            20                  25                  30
Val Lys Ser His Lys Phe Thr Ala Arg Phe Phe Lys Gln Pro Thr Phe
        35                  40                  45
Cys Ser His Cys Thr Asp Phe Ile Trp Gly Ile Gly Lys Gln Gly Leu
    50                  55                  60
Gln Cys Gln Val Cys Ser Phe Val Val His Arg Arg Cys His Glu Phe
65                  70                  75                  80
Val Thr Phe Glu Cys Pro Gly Ala Gly Lys Gly Pro Gln Thr Asp Asp
                85                  90                  95
Pro Arg Asn Lys His Lys Phe Arg Leu His Ser Tyr Ser Ser Pro Thr
            100                 105                 110
Phe Cys Asp His Cys Gly Ser Leu Leu Tyr Gly Leu Val His Gln Gly
        115                 120                 125
```

-continued

```
Met Lys Cys Ser Cys Cys Glu Met Asn Val His Arg Arg Cys Val Arg
            130                 135                 140

Ser Val Pro Ser Leu Cys Gly Val Asp His Thr Glu Arg Arg Gly Arg
145                 150                 155                 160

Leu Gln Leu Glu Ile Arg Ala Pro Thr Ala Asp Glu Ile His Val Thr
                165                 170                 175

Val Gly Glu Ala Arg Asn Leu Ile Pro Met Asp Pro Asn Gly Leu Ser
            180                 185                 190

Asp Pro Tyr Val Lys Leu Lys Leu Ile Pro Asp Pro Arg Asn Leu Thr
                195                 200                 205

Lys Gln Lys Thr Arg Thr Val Lys Ala Thr Leu Asn Pro Val Trp Asn
    210                 215                 220

Glu Thr Phe Val Phe Asn Leu Lys Pro Gly Asp Val Glu Arg Arg Leu
225                 230                 235                 240

Ser Val Glu Val Trp Asp Trp Asp Arg Thr Ser Arg Asn Asp Phe Met
                245                 250                 255

Gly Ala Met Ser Phe Gly Val Ser Glu Leu Leu Lys Ala Pro Val Asp
                260                 265                 270

Gly Trp Tyr Lys Leu Leu Asn Gln Glu Glu Gly Glu Tyr Tyr Asn Val
                275                 280                 285

Pro Val Ala Asp Ala Asp Asn Cys Ser Leu Leu Gln Lys Phe Glu Ala
            290                 295                 300

Cys Asn Tyr Pro Leu Glu Leu Tyr Glu Arg Val Arg Met Gly Pro Ser
305                 310                 315                 320

Ser Ser Pro Ile Pro Ser Pro Ser Pro Thr Asp Pro Lys Arg
                325                 330                 335

Cys Phe Phe Gly Ala Ser Pro Gly Arg Leu His Ile Ser Asp Phe Ser
                340                 345                 350

Phe Leu Met Val Leu Gly Lys Gly Ser Phe Gly Lys Val Met Leu Ala
        355                 360                 365

Glu Arg Arg Gly Ser Asp Glu Leu Tyr Ala Ile Lys Ile Leu Lys Lys
    370                 375                 380

Asp Val Ile Val Gln Asp Asp Val Asp Cys Thr Leu Val Glu Lys
385                 390                 395                 400

Arg Val Leu Ala Leu Gly Gly Arg Gly Pro Gly Gly Arg Pro His Phe
                405                 410                 415

Leu Thr Gln Leu His Ser Thr Phe Gln Thr Pro Asp Arg Leu Tyr Phe
                420                 425                 430

Val Met Glu Tyr Val Thr Gly Gly Asp Leu Met Tyr His Ile Gln Gln
        435                 440                 445

Leu Gly Lys Phe Lys Glu Pro His Ala Ala Phe Tyr Ala Ala Glu Ile
    450                 455                 460

Ala Ile Gly Leu Phe Phe Leu His Asn Gln Gly Ile Ile Tyr Arg Asp
465                 470                 475                 480

Leu Lys Leu Asp Asn Val Met Leu Asp Ala Glu Gly His Ile Lys Ile
                485                 490                 495

Thr Asp Phe Gly Met Cys Lys Glu Asn Val Phe Pro Gly Thr Thr Thr
            500                 505                 510

Arg Thr Phe Cys Gly Thr Pro Asp Tyr Ile Ala Pro Glu Ile Ile Ala
            515                 520                 525

Tyr Gln Pro Tyr Gly Lys Ser Val Asp Trp Trp Ser Phe Gly Val Leu
    530                 535                 540

Leu Tyr Glu Met Leu Ala Gly Gln Pro Pro Phe Asp Gly Glu Asp Glu
```

-continued

```
                545                 550                 555                 560

Glu Glu Leu Phe Gln Ala Ile Met Glu Gln Thr Val Thr Tyr Pro Lys
                    565                 570                 575

Ser Leu Ser Arg Glu Ala Val Ala Ile Cys Lys Gly Phe Leu Thr Lys
                580                 585                 590

His Pro Gly Lys Arg Leu Gly Ser Gly Pro Asp Gly Glu Pro Thr Ile
                595                 600                 605

Arg Ala His Gly Phe Phe Arg Trp Ile Asp Trp Glu Arg Leu Glu Arg
            610                 615                 620

Leu Glu Ile Pro Pro Phe Arg Pro Arg Pro Cys Gly Arg Ser Gly
625                 630                 635                 640

Glu Asn Phe Asp Lys Phe Phe Thr Arg Ala Ala Pro Ala Leu Thr Pro
                    645                 650                 655

Pro Asp Arg Leu Val Leu Ala Ser Ile Asp Gln Ala Asp Phe Gln Gly
                660                 665                 670

Phe Thr Tyr Val Asn Pro Asp Phe Val His Pro Asp Ala Arg Ser Pro
            675                 680                 685

Thr Ser Pro Val Pro Val Pro Val Met
        690                 695
```

<210> SEQ ID NO 168
<211> LENGTH: 676
<212> TYPE: PRT
<213> ORGANISM: Homo sapiens

<400> SEQUENCE: 168

```
Met Ala Pro Phe Leu Arg Ile Ala Phe Asn Ser Tyr Glu Leu Gly Ser
  1               5                  10                  15

Leu Gln Ala Glu Asp Glu Ala Asn Gln Pro Phe Cys Ala Val Lys Met
                 20                  25                  30

Lys Glu Ala Leu Ser Thr Glu Arg Gly Lys Thr Leu Val Gln Lys Lys
             35                  40                  45

Pro Thr Met Tyr Pro Glu Trp Lys Ser Thr Phe Asp Ala His Ile Tyr
         50                  55                  60

Glu Gly Arg Val Ile Gln Ile Val Leu Met Arg Ala Ala Glu Glu Pro
 65                  70                  75                  80

Val Ser Glu Val Thr Val Gly Val Ser Val Leu Ala Glu Arg Cys Lys
                 85                  90                  95

Lys Asn Asn Gly Lys Ala Glu Phe Trp Leu Asp Leu Gln Pro Gln Ala
                100                 105                 110

Lys Val Leu Met Ser Val Gln Tyr Phe Leu Glu Asp Val Asp Cys Lys
            115                 120                 125

Gln Ser Met Arg Ser Glu Asp Glu Ala Lys Phe Pro Thr Met Asn Arg
        130                 135                 140

Arg Gly Ala Ile Lys Gln Ala Lys Ile His Tyr Ile Lys Asn His Glu
145                 150                 155                 160

Phe Ile Ala Thr Phe Phe Gly Gln Pro Thr Phe Cys Ser Val Cys Lys
                165                 170                 175

Asp Phe Val Trp Gly Leu Asn Lys Gln Gly Tyr Lys Cys Arg Gln Cys
            180                 185                 190

Asn Ala Ala Ile His Lys Lys Cys Ile Asp Lys Ile Ile Gly Arg Cys
        195                 200                 205

Thr Gly Thr Ala Ala Asn Ser Arg Asp Thr Ile Phe Gln Lys Glu Arg
    210                 215                 220
```

```
Phe Asn Ile Asp Met Pro His Arg Phe Lys Val His Asn Tyr Met Ser
225                 230                 235                 240

Pro Thr Phe Cys Asp His Cys Gly Ser Leu Leu Trp Gly Leu Val Lys
            245                 250                 255

Gln Gly Leu Lys Cys Glu Asp Cys Gly Met Asn Val His His Lys Cys
            260                 265                 270

Arg Glu Lys Val Ala Asn Leu Cys Gly Ile Asn Gln Lys Leu Leu Ala
            275                 280                 285

Glu Ala Leu Asn Gln Val Thr Gln Arg Ala Ser Arg Arg Ser Asp Ser
        290                 295                 300

Ala Ser Ser Glu Pro Val Gly Ile Tyr Gln Gly Phe Glu Lys Lys Thr
305                 310                 315                 320

Gly Val Ala Gly Glu Asp Met Gln Asp Asn Ser Gly Thr Tyr Gly Lys
                325                 330                 335

Ile Trp Glu Gly Ser Ser Lys Cys Asn Ile Asn Asn Phe Ile Phe His
                340                 345                 350

Lys Val Leu Gly Lys Gly Ser Phe Gly Lys Val Leu Leu Gly Glu Leu
            355                 360                 365

Lys Gly Arg Gly Glu Tyr Phe Ala Ile Lys Ala Leu Lys Lys Asp Val
        370                 375                 380

Val Leu Ile Asp Asp Asp Val Glu Cys Thr Met Val Glu Lys Arg Val
385                 390                 395                 400

Leu Thr Leu Ala Ala Glu Asn Pro Phe Leu Thr His Leu Ile Cys Thr
                405                 410                 415

Phe Gln Thr Lys Asp His Leu Phe Phe Val Met Glu Phe Leu Asn Gly
                420                 425                 430

Gly Asp Leu Met Tyr His Ile Gln Asp Lys Gly Arg Phe Glu Leu Tyr
            435                 440                 445

Arg Ala Thr Phe Tyr Ala Ala Glu Ile Met Cys Gly Leu Gln Phe Leu
450                 455                 460

His Ser Lys Gly Ile Ile Tyr Arg Asp Leu Lys Leu Asp Asn Val Leu
465                 470                 475                 480

Leu Asp Arg Asp Gly His Ile Lys Ile Ala Asp Phe Gly Met Cys Lys
                485                 490                 495

Glu Asn Ile Phe Gly Glu Ser Arg Ala Ser Thr Phe Cys Gly Thr Pro
                500                 505                 510

Asp Tyr Ile Ala Pro Glu Ile Leu Gln Gly Leu Lys Tyr Thr Phe Ser
            515                 520                 525

Val Asp Trp Trp Ser Phe Gly Val Leu Leu Tyr Glu Met Leu Ile Gly
            530                 535                 540

Gln Ser Pro Phe His Gly Asp Asp Glu Asp Glu Leu Phe Glu Ser Ile
545                 550                 555                 560

Arg Val Asp Thr Pro His Tyr Pro Arg Trp Ile Thr Lys Glu Ser Lys
                565                 570                 575

Asp Ile Leu Glu Lys Leu Phe Glu Arg Glu Pro Thr Lys Arg Leu Gly
            580                 585                 590

Val Thr Gly Asn Ile Lys Ile His Pro Phe Phe Lys Thr Ile Asn Trp
            595                 600                 605

Thr Leu Leu Glu Lys Arg Arg Leu Glu Pro Pro Phe Arg Pro Lys Val
            610                 615                 620

Lys Ser Pro Arg Asp Tyr Ser Asn Phe Asp Gln Glu Phe Leu Asn Glu
625                 630                 635                 640

Lys Ala Arg Leu Ser Tyr Ser Asp Lys Asn Leu Ile Asp Ser Met Asp
```

-continued

```
                    645                 650                 655
Gln Ser Ala Phe Ala Gly Phe Ser Phe Val Asn Pro Lys Phe Glu His
                660                 665                 670

Leu Leu Glu Asp
        675

<210> SEQ ID NO 169
<211> LENGTH: 737
<212> TYPE: PRT
<213> ORGANISM: Homo sapiens

<400> SEQUENCE: 169

Met Val Val Phe Asn Gly Leu Leu Lys Ile Lys Ile Cys Glu Ala Val
 1               5                  10                  15

Ser Leu Lys Pro Thr Ala Trp Ser Leu Arg His Ala Val Gly Pro Arg
                20                  25                  30

Pro Gln Thr Phe Leu Leu Asp Pro Tyr Ile Ala Leu Asn Val Asp Asp
            35                  40                  45

Ser Arg Ile Gly Gln Thr Ala Thr Lys Gln Lys Thr Asn Ser Pro Ala
        50                  55                  60

Trp His Asp Glu Phe Val Thr Asp Val Cys Asn Gly Arg Lys Ile Glu
 65                 70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
                100                 105                 110

Phe Glu Asp Trp Ile Asp Leu Glu Pro Glu Gly Arg Val Tyr Val Ile
            115                 120                 125

Ile Asp Leu Ser Gly Ser Ser Gly Glu Ala Pro Lys Asp Asn Glu Glu
        130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175

Leu Arg Gln Pro Thr Tyr Cys Ser His Cys Arg Asp Phe Ile Trp Gly
                180                 185                 190

Val Ile Gly Lys Gln Gly Tyr Gln Cys Gln Val Cys Thr Cys Val Val
            195                 200                 205

His Lys Arg Cys His Glu Leu Ile Ile Thr Lys Cys Ala Gly Leu Lys
        210                 215                 220

Lys Gln Glu Thr Pro Asp Gln Val Gly Ser Gln Arg Phe Ser Val Asn
225                 230                 235                 240

Met Pro His Lys Phe Gly Ile His Asn Tyr Lys Val Pro Thr Phe Cys
                245                 250                 255

Asp His Cys Gly Ser Leu Leu Trp Gly Leu Leu Arg Gln Gly Leu Gln
            260                 265                 270

Cys Lys Val Cys Lys Met Asn Val His Arg Arg Cys Glu Thr Asn Val
        275                 280                 285

Ala Pro Asn Cys Gly Val Asp Ala Arg Gly Ile Ala Lys Val Leu Ala
    290                 295                 300

Asp Leu Gly Val Thr Pro Asp Lys Ile Thr Asn Ser Gly Gln Arg Arg
305                 310                 315                 320

Lys Lys Leu Ile Ala Gly Ala Glu Ser Pro Gln Pro Ala Ser Gly Ser
                325                 330                 335
```

-continued

```
Ser Pro Ser Glu Glu Asp Arg Ser Lys Ser Ala Pro Thr Ser Pro Cys
            340                 345                 350

Asp Gln Glu Ile Lys Glu Leu Glu Asn Asn Ile Arg Lys Ala Leu Ser
            355                 360                 365

Phe Asp Asn Arg Gly Glu His Arg Ala Ala Ser Ser Pro Asp Gly
            370                 375                 380

Gln Leu Met Ser Pro Glu Asn Gly Glu Val Arg Gln Gly Gln Ala
385                 390                 395                 400

Lys Arg Leu Gly Leu Asp Glu Phe Asn Phe Ile Lys Val Leu Gly Lys
                405                 410                 415

Gly Ser Phe Gly Lys Val Met Leu Ala Glu Leu Lys Gly Lys Asp Glu
            420                 425                 430

Val Tyr Ala Val Lys Val Leu Lys Lys Asp Val Ile Leu Gln Asp Asp
            435                 440                 445

Asp Val Asp Cys Thr Met Thr Glu Lys Arg Ile Leu Ala Leu Ala Arg
450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
                485                 490                 495

Gln Ile Gln Arg Ser Arg Lys Phe Asp Glu Pro Arg Ser Arg Phe Tyr
            500                 505                 510

Ala Ala Glu Val Thr Ser Ala Leu Met Phe Leu His Gln His Gly Val
            515                 520                 525

Ile Tyr Arg Asp Leu Lys Leu Asp Asn Ile Leu Leu Asp Ala Glu Gly
            530                 535                 540

His Cys Lys Leu Ala Asp Phe Gly Met Cys Lys Glu Gly Ile Leu Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
            580                 585                 590

Leu Gly Val Leu Met Tyr Glu Met Met Ala Gly Gln Pro Pro Phe Glu
            595                 600                 605

Ala Asp Asn Glu Asp Asp Leu Phe Glu Ser Ile Leu His Asp Asp Val
            610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ser Gln
                645                 650                 655

Asn Gly Glu Asp Ala Ile Lys Gln His Pro Phe Phe Lys Glu Ile Asp
            660                 665                 670

Trp Val Leu Leu Glu Gln Lys Lys Ile Lys Pro Pro Phe Lys Pro Arg
            675                 680                 685

Ile Lys Thr Lys Arg Asp Val Asn Asn Phe Asp Gln Asp Phe Thr Arg
            690                 695                 700

Glu Glu Pro Val Leu Thr Leu Val Asp Glu Ala Ile Val Lys Gln Ile
705                 710                 715                 720

Asn Gln Glu Glu Phe Lys Gly Phe Ser Tyr Phe Gly Glu Asp Leu Met
                725                 730                 735

Pro
```

<210> SEQ ID NO 170

<211> LENGTH: 682
<212> TYPE: PRT
<213> ORGANISM: Homo sapiens

<400> SEQUENCE: 170

```
Met Ser Ser Gly Thr Met Lys Phe Asn Gly Tyr Leu Arg Val Arg Ile
 1               5                  10                  15

Gly Glu Ala Val Gly Leu Gln Pro Thr Arg Trp Ser Leu Arg His Ser
            20                  25                  30

Leu Phe Lys Lys Gly His Gln Leu Leu Asp Pro Tyr Leu Thr Val Ser
        35                  40                  45

Val Asp Gln Val Arg Val Gly Gln Thr Ser Thr Lys Gln Lys Thr Asn
    50                  55                  60

Lys Pro Thr Tyr Asn Glu Glu Phe Cys Ala Asn Val Thr Asp Gly Gly
 65                  70                  75                  80

His Leu Glu Leu Ala Val Phe His Glu Thr Pro Leu Gly Tyr Asp Phe
                85                  90                  95

Val Ala Asn Cys Thr Leu Gln Phe Gln Glu Leu Val Gly Thr Thr Gly
            100                 105                 110

Ala Ser Asp Thr Phe Glu Gly Trp Val Asp Leu Glu Pro Glu Gly Lys
        115                 120                 125

Val Phe Val Ile Thr Leu Thr Gly Ser Phe Thr Glu Ala Thr Leu
    130                 135                 140

Gln Arg Asp Arg Ile Phe Lys His Phe Thr Arg Lys Arg Gln Arg Ala
145                 150                 155                 160

Met Arg Arg Arg Val His Gln Ile Asn Gly His Lys Phe Met Ala Thr
                165                 170                 175

Tyr Leu Arg Gln Pro Thr Tyr Cys Ser His Cys Arg Glu Phe Ile Trp
            180                 185                 190

Gly Val Phe Gly Lys Gln Gly Tyr Gln Cys Gln Val Cys Thr Cys Val
        195                 200                 205

Val His Lys Arg Cys His His Leu Ile Val Thr Ala Cys Thr Cys Gln
    210                 215                 220

Asn Asn Ile Asn Lys Val Asp Ser Lys Ile Ala Glu Gln Arg Phe Gly
225                 230                 235                 240

Ile Asn Ile Pro His Lys Phe Ser Ile His Asn Tyr Lys Val Pro Thr
                245                 250                 255

Phe Cys Asp His Cys Gly Ser Leu Leu Trp Gly Ile Met Arg Gln Gly
            260                 265                 270

Leu Gln Cys Lys Ile Cys Lys Met Asn Val His Ile Arg Cys Gln Ala
        275                 280                 285

Asn Val Ala Pro Asn Cys Gly Val Asn Ala Val Glu Leu Ala Lys Thr
    290                 295                 300

Leu Ala Gly Met Gly Leu Gln Pro Gly Asn Ile Ser Pro Thr Ser Lys
305                 310                 315                 320

Leu Val Ser Arg Ser Thr Leu Arg Arg Gln Gly Lys Glu Ser Ser Lys
                325                 330                 335

Glu Gly Asn Gly Ile Gly Val Asn Ser Ser Asn Arg Leu Gly Ile Asp
            340                 345                 350

Asn Phe Glu Phe Ile Arg Val Leu Gly Lys Gly Ser Phe Gly Lys Val
        355                 360                 365

Met Leu Ala Arg Val Lys Glu Thr Gly Asp Leu Tyr Ala Val Lys Val
    370                 375                 380

Leu Lys Lys Asp Val Ile Leu Leu Asp Asp Asp Val Glu Cys Thr Met
```

-continued

```
            385                 390                 395                 400
Thr Glu Lys Arg Ile Leu Ser Leu Ala Arg Asn His Pro Phe Leu Thr
                    405                 410                 415
Gln Leu Phe Cys Cys Phe Gln Thr Pro Asp Arg Leu Phe Phe Val Met
                420                 425                 430
Glu Phe Val Asn Gly Gly Asp Leu Met Phe His Ile Gln Lys Ser Arg
            435                 440                 445
Arg Phe Asp Glu Ala Arg Ala Arg Phe Tyr Ala Ala Glu Ile Ile Ser
        450                 455                 460
Ala Leu Met Phe Leu His Asp Lys Gly Ile Ile Tyr Arg Asp Leu Lys
465                 470                 475                 480
Leu Asp Asn Val Leu Leu Asp His Glu Gly His Cys Lys Leu Ala Asp
                485                 490                 495
Phe Gly Met Cys Lys Glu Gly Ile Cys Asn Gly Val Thr Thr Ala Thr
                500                 505                 510
Phe Cys Gly Thr Pro Asp Tyr Ile Ala Pro Glu Ile Leu Gln Glu Met
            515                 520                 525
Leu Tyr Gly Pro Ala Val Asp Trp Trp Ala Met Gly Val Leu Leu Tyr
        530                 535                 540
Glu Met Leu Cys Gly His Ala Pro Phe Glu Ala Glu Asn Glu Asp Asp
545                 550                 555                 560
Leu Phe Glu Ala Ile Leu Asn Asp Glu Val Val Tyr Pro Thr Trp Leu
                565                 570                 575
His Glu Asp Ala Thr Gly Ile Leu Lys Ser Phe Met Thr Lys Asn Pro
            580                 585                 590
Thr Met Arg Leu Gly Ser Leu Thr Gln Gly Gly Glu His Ala Ile Leu
        595                 600                 605
Arg His Pro Phe Phe Lys Glu Ile Asp Trp Ala Gln Leu Asn His Arg
    610                 615                 620
Gln Ile Glu Pro Pro Phe Arg Pro Arg Ile Lys Ser Arg Glu Asp Val
625                 630                 635                 640
Ser Asn Phe Asp Pro Asp Phe Ile Lys Glu Glu Pro Val Leu Thr Pro
                645                 650                 655
Ile Asp Glu Gly His Leu Pro Met Ile Asn Gln Asp Glu Phe Arg Asn
            660                 665                 670
Phe Ser Tyr Val Ser Pro Glu Leu Gln Pro
        675                 680

<210> SEQ ID NO 171
<211> LENGTH: 706
<212> TYPE: PRT
<213> ORGANISM: Homo sapiens

<400> SEQUENCE: 171

Met Ser Pro Phe Leu Arg Ile Gly Leu Ser Asn Phe Asp Cys Gly Ser
1               5                   10                  15
Cys Gln Ser Cys Gln Gly Glu Ala Val Asn Pro Tyr Cys Ala Val Leu
                20                  25                  30
Val Lys Glu Tyr Val Glu Ser Glu Asn Gly Gln Met Tyr Ile Gln Lys
            35                  40                  45
Lys Pro Thr Met Tyr Pro Pro Trp Asp Ser Thr Phe Asp Ala His Ile
        50                  55                  60
Asn Lys Gly Arg Val Met Gln Ile Ile Val Lys Gly Lys Asn Val Asp
65                  70                  75                  80
```

```
Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125

Lys Asp Met Asn Glu Phe Glu Thr Glu Gly Phe Phe Ala Leu His Gln
    130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
    210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270

Cys Gln Thr Lys Val Ala Asn Leu Cys Gly Ile Asn Gln Lys Leu Met
        275                 280                 285

Ala Glu Ala Leu Ala Met Ile Glu Ser Thr Gln Gln Ala Arg Cys Leu
    290                 295                 300

Arg Asp Thr Glu Gln Ile Phe Arg Glu Gly Pro Val Glu Ile Gly Leu
305                 310                 315                 320

Pro Cys Ser Ile Lys Asn Glu Ala Arg Pro Pro Cys Leu Pro Thr Pro
                325                 330                 335

Gly Lys Arg Glu Pro Gln Gly Ile Ser Trp Glu Ser Pro Leu Asp Glu
            340                 345                 350

Val Asp Lys Met Cys His Leu Pro Glu Pro Glu Leu Asn Lys Glu Arg
        355                 360                 365

Pro Ser Leu Gln Ile Lys Leu Lys Ile Glu Asp Phe Ile Leu His Lys
    370                 375                 380

Met Leu Gly Lys Gly Ser Phe Gly Lys Val Phe Leu Ala Glu Phe Lys
385                 390                 395                 400

Lys Thr Asn Gln Phe Phe Ala Ile Lys Ala Leu Lys Lys Asp Val Val
                405                 410                 415

Leu Met Asp Asp Asp Val Glu Cys Thr Met Val Glu Lys Arg Val Leu
            420                 425                 430

Ser Leu Ala Trp Glu His Pro Phe Leu Thr His Met Phe Cys Thr Phe
        435                 440                 445

Gln Thr Lys Glu Asn Leu Phe Phe Val Met Glu Tyr Leu Asn Gly Gly
    450                 455                 460

Asp Leu Met Tyr His Ile Gln Ser Cys His Lys Phe Asp Leu Ser Arg
465                 470                 475                 480

Ala Thr Phe Tyr Ala Ala Glu Ile Ile Leu Gly Leu Gln Phe Leu His
                485                 490                 495

Ser Lys Gly Ile Val Tyr Arg Asp Leu Lys Leu Asp Asn Ile Leu Leu
```

```
                500                 505                 510
Asp Lys Asp Gly His Ile Lys Ile Ala Asp Phe Gly Met Cys Lys Glu
            515                 520                 525
Asn Met Leu Gly Asp Ala Lys Thr Asn Thr Phe Cys Gly Thr Pro Asp
            530                 535                 540
Tyr Ile Ala Pro Glu Ile Leu Leu Gly Gln Lys Tyr Asn His Ser Val
545                 550                 555                 560
Asp Trp Trp Ser Phe Gly Val Leu Leu Tyr Glu Met Leu Ile Gly Gln
                565                 570                 575
Ser Pro Phe His Gly Gln Asp Glu Glu Glu Leu Phe His Ser Ile Arg
            580                 585                 590
Met Asp Asn Pro Phe Tyr Pro Arg Trp Leu Glu Lys Glu Ala Lys Asp
            595                 600                 605
Leu Leu Val Lys Leu Phe Val Arg Glu Pro Glu Lys Arg Leu Gly Val
            610                 615                 620
Arg Gly Asp Ile Arg Gln His Pro Leu Phe Arg Glu Ile Asn Trp Glu
625                 630                 635                 640
Glu Leu Glu Arg Lys Glu Ile Asp Pro Pro Phe Arg Pro Lys Val Lys
                645                 650                 655
Ser Pro Phe Asp Cys Ser Asn Phe Asp Lys Glu Phe Leu Asn Glu Lys
            660                 665                 670
Pro Arg Leu Ser Phe Ala Asp Arg Ala Leu Ile Asn Ser Met Asp Gln
            675                 680                 685
Asn Met Phe Arg Asn Phe Ser Phe Met Asn Pro Gly Met Glu Arg Leu
            690                 695                 700
Glu Ser
705

<210> SEQ ID NO 172
<211> LENGTH: 587
<212> TYPE: PRT
<213> ORGANISM: Homo sapiens

<400> SEQUENCE: 172

Met Ser His Thr Val Ala Gly Gly Ser Gly Asp His Ser His Gln
1               5                   10                  15
Val Arg Val Lys Ala Tyr Tyr Arg Gly Asp Ile Met Ile Thr His Phe
            20                  25                  30
Glu Pro Ser Ile Ser Phe Glu Gly Leu Cys Asn Glu Val Arg Asp Met
            35                  40                  45
Cys Ser Phe Asp Asn Glu Gln Leu Phe Thr Met Lys Trp Ile Asp Glu
        50                  55                  60
Glu Gly Asp Pro Cys Thr Val Ser Ser Gln Leu Glu Leu Glu Glu Ala
65                  70                  75                  80
Phe Arg Leu Tyr Glu Leu Asn Lys Asp Ser Glu Leu Leu Ile His Val
                85                  90                  95
Phe Pro Cys Val Pro Glu Arg Pro Gly Met Pro Cys Pro Gly Glu Asp
            100                 105                 110
Lys Ser Ile Tyr Arg Arg Gly Ala Arg Arg Trp Arg Lys Leu Tyr Cys
            115                 120                 125
Ala Asn Gly His Thr Phe Gln Ala Lys Arg Phe Asn Arg Arg Ala His
            130                 135                 140
Cys Ala Ile Cys Thr Asp Arg Ile Trp Gly Leu Gly Arg Gln Gly Tyr
145                 150                 155                 160
```

-continued

```
Lys Cys Ile Asn Cys Lys Leu Leu Val His Lys Lys Cys His Lys Leu
                165                 170                 175
Val Thr Ile Glu Cys Gly Arg His Ser Leu Pro Gln Glu Pro Val Met
            180                 185                 190
Pro Met Asp Gln Ser Ser Met His Ser Asp His Ala Gln Thr Val Ile
        195                 200                 205
Pro Tyr Asn Pro Ser Ser His Glu Ser Leu Asp Gln Val Gly Glu Glu
    210                 215                 220
Lys Glu Ala Met Asn Thr Arg Glu Ser Gly Lys Ala Ser Ser Ser Leu
225                 230                 235                 240
Gly Leu Gln Asp Phe Asp Leu Leu Arg Val Ile Arg Gly Ser Tyr
                245                 250                 255
Ala Lys Val Leu Leu Val Arg Leu Lys Lys Thr Asp Arg Ile Tyr Ala
            260                 265                 270
Met Lys Val Val Lys Lys Glu Leu Val Asn Asp Asp Glu Asp Ile Asp
        275                 280                 285
Trp Val Gln Thr Glu Lys His Val Phe Glu Gln Ala Ser Asn His Pro
    290                 295                 300
Phe Leu Val Gly Leu His Ser Cys Phe Gln Thr Glu Ser Arg Leu Phe
305                 310                 315                 320
Phe Val Ile Glu Tyr Val Asn Gly Gly Asp Leu Met Phe His Met Gln
                325                 330                 335
Arg Gln Arg Lys Leu Pro Glu Glu His Ala Arg Phe Tyr Ser Ala Glu
            340                 345                 350
Ile Ser Leu Ala Leu Asn Tyr Leu His Glu Arg Gly Ile Ile Tyr Arg
        355                 360                 365
Asp Leu Lys Leu Asp Asn Val Leu Leu Asp Ser Glu Gly His Ile Lys
    370                 375                 380
Leu Thr Asp Tyr Gly Met Cys Lys Glu Gly Leu Arg Pro Gly Asp Thr
385                 390                 395                 400
Thr Ser Thr Phe Cys Gly Thr Pro Asn Tyr Ile Ala Pro Glu Ile Leu
                405                 410                 415
Arg Gly Glu Asp Tyr Gly Phe Ser Val Asp Trp Trp Ala Leu Gly Val
            420                 425                 430
Leu Met Phe Glu Met Met Ala Gly Arg Ser Pro Phe Asp Ile Val Gly
        435                 440                 445
Ser Ser Asp Asn Pro Asp Gln Asn Thr Glu Asp Tyr Leu Phe Gln Val
    450                 455                 460
Ile Leu Glu Lys Gln Ile Arg Ile Pro Arg Ser Leu Ser Val Lys Ala
465                 470                 475                 480
Ala Ser Val Leu Lys Ser Phe Leu Asn Lys Asp Pro Lys Glu Arg Leu
                485                 490                 495
Gly Cys His Pro Gln Thr Gly Phe Ala Asp Ile Gln Gly His Pro Phe
            500                 505                 510
Phe Arg Asn Val Asp Trp Asp Met Met Glu Gln Lys Gln Val Val Pro
        515                 520                 525
Pro Phe Lys Pro Asn Ile Ser Gly Glu Phe Gly Leu Asp Asn Phe Asp
    530                 535                 540
Ser Gln Phe Thr Asn Glu Pro Val Gln Leu Thr Pro Asp Asp Asp Asp
545                 550                 555                 560
Ile Val Arg Lys Ile Asp Gln Ser Glu Phe Glu Gly Phe Glu Tyr Ile
                565                 570                 575
Asn Pro Leu Leu Met Ser Ala Glu Glu Cys Val
```

-continued

```
                580                 585

<210> SEQ ID NO 173
<211> LENGTH: 912
<212> TYPE: PRT
<213> ORGANISM: Homo sapiens

<400> SEQUENCE: 173

Met Ser Ala Pro Pro Val Leu Arg Pro Pro Ser Pro Leu Leu Pro Val
  1               5                  10                  15

Ala Ala Ala Ala Ala Ala Ala Ala Leu Val Pro Gly Ser Gly
             20                  25                  30

Pro Gly Pro Ala Pro Phe Leu Ala Pro Val Ala Pro Val Gly Gly
         35                  40                  45

Ile Ser Phe His Leu Gln Ile Gly Leu Ser Arg Glu Pro Val Leu Leu
 50                  55                  60

Leu Gln Asp Ser Ser Gly Asp Tyr Ser Leu Ala His Val Arg Glu Met
 65                  70                  75                  80

Ala Cys Ser Ile Val Asp Gln Lys Phe Pro Glu Cys Gly Phe Tyr Gly
                 85                  90                  95

Met Tyr Asp Lys Ile Leu Leu Phe Arg His Asp Pro Thr Ser Glu Asn
            100                 105                 110

Ile Leu Gln Leu Val Lys Ala Ala Ser Asp Ile Gln Glu Gly Asp Leu
        115                 120                 125

Ile Glu Val Val Leu Ser Arg Ser Ala Thr Phe Glu Asp Phe Gln Ile
    130                 135                 140

Arg Pro His Ala Leu Phe Val His Ser Tyr Arg Ala Pro Ala Phe Cys
145                 150                 155                 160

Asp His Cys Gly Glu Met Leu Trp Gly Leu Val Arg Gln Gly Leu Lys
                165                 170                 175

Cys Glu Gly Cys Gly Leu Asn Tyr His Lys Arg Cys Ala Phe Lys Ile
            180                 185                 190

Pro Asn Asn Cys Ser Gly Val Arg Arg Arg Arg Leu Ser Asn Val Ser
        195                 200                 205

Leu Thr Gly Val Ser Thr Ile Arg Thr Ser Ser Ala Glu Leu Ser Thr
    210                 215                 220

Ser Ala Pro Asp Glu Pro Leu Leu Gln Lys Ser Pro Ser Glu Ser Phe
225                 230                 235                 240

Ile Gly Arg Glu Lys Arg Ser Asn Ser Gln Ser Tyr Ile Gly Arg Pro
                245                 250                 255

Ile His Leu Asp Lys Ile Leu Met Ser Lys Val Lys Val Pro His Thr
            260                 265                 270

Phe Val Ile His Ser Tyr Thr Arg Pro Thr Val Cys Gln Tyr Cys Lys
        275                 280                 285

Lys Leu Leu Lys Gly Leu Phe Arg Gln Gly Leu Gln Cys Lys Asp Cys
    290                 295                 300

Arg Phe Asn Cys His Lys Arg Cys Ala Pro Lys Val Pro Asn Asn Cys
305                 310                 315                 320

Leu Gly Glu Val Thr Ile Asn Gly Asp Leu Leu Ser Pro Gly Ala Glu
                325                 330                 335

Ser Asp Val Val Met Glu Glu Gly Ser Asp Asp Asn Asp Ser Glu Arg
            340                 345                 350

Asn Ser Gly Leu Met Asp Asp Met Glu Glu Ala Met Val Gln Asp Ala
        355                 360                 365
```

-continued

```
Glu Met Ala Met Ala Glu Cys Gln Asn Asp Ser Gly Glu Met Gln Asp
    370                 375                 380
Pro Asp Pro Asp His Glu Asp Ala Asn Arg Thr Ile Ser Pro Ser Thr
385                 390                 395                 400
Ser Asn Asn Ile Pro Leu Met Arg Val Val Gln Ser Val Lys His Thr
                405                 410                 415
Lys Arg Lys Ser Ser Thr Val Met Lys Glu Gly Trp Met Val His Tyr
            420                 425                 430
Thr Ser Lys Asp Thr Leu Arg Lys Arg His Tyr Trp Arg Leu Asp Ser
        435                 440                 445
Lys Cys Ile Thr Leu Phe Gln Asn Asp Thr Gly Ser Arg Tyr Tyr Lys
    450                 455                 460
Glu Ile Pro Leu Ser Glu Ile Leu Ser Leu Glu Pro Val Lys Thr Ser
465                 470                 475                 480
Ala Leu Ile Pro Asn Gly Ala Asn Pro His Cys Phe Glu Ile Thr Thr
                485                 490                 495
Ala Asn Val Val Tyr Tyr Val Gly Glu Asn Val Val Asn Pro Ser Ser
            500                 505                 510
Pro Ser Pro Asn Asn Ser Val Leu Thr Ser Gly Val Gly Ala Asp Val
        515                 520                 525
Ala Arg Met Trp Glu Ile Ala Ile Gln His Ala Leu Met Pro Val Ile
    530                 535                 540
Pro Lys Gly Ser Ser Val Gly Thr Gly Thr Asn Leu His Arg Asp Ile
545                 550                 555                 560
Ser Val Ser Ile Ser Val Ser Asn Cys Gln Ile Gln Glu Asn Val Asp
                565                 570                 575
Ile Ser Thr Val Tyr Gln Ile Phe Pro Asp Glu Val Leu Gly Ser Gly
            580                 585                 590
Gln Phe Gly Ile Val Tyr Gly Gly Lys His Arg Lys Thr Gly Arg Asp
        595                 600                 605
Val Ala Ile Lys Ile Ile Asp Lys Leu Arg Phe Pro Thr Lys Gln Glu
    610                 615                 620
Ser Gln Leu Arg Asn Glu Val Ala Ile Leu Gln Asn Leu His His Pro
625                 630                 635                 640
Gly Val Val Asn Leu Glu Cys Met Phe Glu Thr Pro Glu Arg Val Phe
                645                 650                 655
Val Val Met Glu Lys Leu His Gly Asp Met Leu Glu Met Ile Leu Ser
            660                 665                 670
Ser Glu Lys Gly Arg Leu Pro Glu His Ile Thr Lys Phe Leu Ile Thr
        675                 680                 685
Gln Ile Leu Val Ala Leu Arg His Leu His Phe Lys Asn Ile Val His
    690                 695                 700
Cys Asp Leu Lys Pro Glu Asn Val Leu Leu Ala Ser Ala Asp Pro Phe
705                 710                 715                 720
Pro Gln Val Lys Leu Cys Asp Phe Gly Phe Ala Arg Ile Ile Gly Glu
                725                 730                 735
Lys Ser Phe Arg Arg Ser Val Val Gly Thr Pro Ala Tyr Leu Ala Pro
            740                 745                 750
Glu Val Leu Arg Asn Lys Gly Tyr Asn Arg Ser Leu Asp Met Trp Ser
        755                 760                 765
Val Gly Val Ile Ile Tyr Val Ser Leu Ser Gly Thr Phe Pro Phe Asn
    770                 775                 780
Glu Asp Glu Asp Ile His Asp Gln Ile Gln Asn Ala Ala Phe Met Tyr
```

-continued

```
785                     790                     795                     800
Pro Pro Asn Pro Trp Lys Glu Ile Ser His Glu Ala Ile Asp Leu Ile
            805                     810                     815

Asn Asn Leu Leu Gln Val Lys Met Arg Lys Arg Tyr Ser Val Asp Lys
            820                     825                     830

Thr Leu Ser His Pro Trp Leu Gln Asp Tyr Gln Thr Trp Leu Asp Leu
            835                     840                     845

Arg Glu Leu Glu Cys Lys Ile Gly Glu Arg Tyr Ile Thr His Glu Ser
        850                     855                     860

Asp Asp Leu Arg Trp Glu Lys Tyr Ala Gly Glu Gln Arg Leu Gln Tyr
865                     870                     875                     880

Pro Thr His Leu Ile Asn Pro Ser Ala Ser His Ser Asp Thr Pro Glu
                885                     890                     895

Thr Glu Glu Thr Glu Met Lys Ala Leu Gly Glu Arg Val Ser Ile Leu
            900                     905                     910
```